US010702860B2

(12) United States Patent
Grison et al.

(10) Patent No.: US 10,702,860 B2
(45) Date of Patent: Jul. 7, 2020

(54) USE OF CERTAIN MANGANESE-ACCUMULATING PLANTS FOR CARRYING OUT ORGANIC CHEMISTRY REACTIONS

(71) Applicants: CENTRE NATIONAL DE LA RECHERCHE SCIENTIFIQUE, Paris (FR); UNIVERSITE MONTPELLIER 2 SCIENCES ET TECHNIQUES, Montpellier (FR)

(72) Inventors: Claude Grison, Castelnau-le-Lez (FR); Vincent Escande, Montpellier (FR)

(73) Assignees: CENTRE NATIONAL DE LA RECHERCHE SCIENTIFIQUE, Paris (FR); UNIVERSITE MONTPELLIER 2 SCIENCES ET TECHNIQUES, Montpellier (FR)

(*) Notice: Subject to any disclaimer, the term of this patent is extended or adjusted under 35 U.S.C. 154(b) by 174 days.

(21) Appl. No.: 14/416,404

(22) PCT Filed: Jul. 23, 2013

(86) PCT No.: PCT/FR2013/051772
§ 371 (c)(1),
(2) Date: Jan. 22, 2015

(87) PCT Pub. No.: WO2014/016509
PCT Pub. Date: Jan. 30, 2014

(65) Prior Publication Data
US 2015/0174566 A1    Jun. 25, 2015

(30) Foreign Application Priority Data
Jul. 23, 2012  (FR) ..................... 12/57135

(51) Int. Cl.
*B01J 31/22*  (2006.01)
*B01J 37/06*  (2006.01)
*B01J 37/08*  (2006.01)
*B01J 37/00*  (2006.01)
*B01J 23/34*  (2006.01)
*B01J 37/36*  (2006.01)
*B09C 1/10*  (2006.01)
*B01J 23/889*  (2006.01)
*B01J 37/14*  (2006.01)
*B01J 37/30*  (2006.01)
*B01J 37/34*  (2006.01)
*C07C 1/20*  (2006.01)
*C07C 5/367*  (2006.01)
*C07C 45/29*  (2006.01)
(Continued)

(52) U.S. Cl.
CPC .......... *B01J 31/2295* (2013.01); *B01J 23/34* (2013.01); *B01J 23/8892* (2013.01); *B01J 37/009* (2013.01); *B01J 37/0036* (2013.01); *B01J 37/0072* (2013.01); *B01J 37/06* (2013.01); *B01J 37/082* (2013.01); *B01J 37/14* (2013.01); *B01J 37/30* (2013.01); *B01J 37/346* (2013.01); *B01J 37/36* (2013.01); *B09C 1/10* (2013.01); *C07C 1/20* (2013.01); *C07C 5/367* (2013.01); *C07C 45/29* (2013.01); *C07C 49/807* (2013.01); *C07C 67/307* (2013.01); *C07C 211/50* (2013.01); *C07C 245/08* (2013.01); *C07D 213/80* (2013.01); *C07D 307/30* (2013.01); *C07D 307/68* (2013.01); *C07D 401/04* (2013.01); *C07D 403/14* (2013.01); *C07D 407/04* (2013.01); *B01J 2231/005* (2013.01); *B01J 2531/72* (2013.01)

(58) Field of Classification Search
CPC ........ B01J 31/2295; B01J 23/80; B01J 31/08; B01J 21/16; B01J 21/08; B01J 23/34; B01J 23/8892; B01J 37/0036; B01J 37/0072; B01J 37/009; B01J 37/06; B01J 37/082; B01J 37/14; B01J 37/30; B01J 37/346; B01J 37/36; C07C 1/20; C07C 5/367; C07C 45/29; C07C 45/46; C07C 49/807; C07C 41/22; C07C 67/08; C07C 67/307; C07C 211/50; C07C 245/08; C07C 231/02; C07C 67/347; C07C 2101/16; C07C 2102/14; C07D 213/80; C07D 307/30; C07D 307/68; C07D 333/28; C07D 223/12; C07D 401/04; C07D 403/14; C07D 407/04; C07D 487/22; C01F 7/188; C07H 3/02; B09C 1/10
See application file for complete search history.

(56) References Cited

U.S. PATENT DOCUMENTS 4,525,218 A    6/1985  Chen et al.
2005/0217174 A1  10/2005  Angel et al.
(Continued)

FOREIGN PATENT DOCUMENTS

CN    101 381 351 A    3/2009
EP    1 806 177 A1    7/2007
(Continued)

OTHER PUBLICATIONS

Baker et al., Terrestrial Higher Plants which Hyperaccumulate Metallic Elements—A Review of their Distribution, Ecology and Phytochemistry, 1989, Biorecovery, vol. 1, pp. 81-126.*
(Continued)

*Primary Examiner* — James A Fiorito
(74) *Attorney, Agent, or Firm* — Young & Thompson

(57) ABSTRACT

The use, after heat treatment, of manganese accumulating plants for carrying out chemical reactions.

21 Claims, No Drawings

(51) Int. Cl.

| | |
|---|---|
| C07C 49/807 | (2006.01) |
| C07C 67/307 | (2006.01) |
| C07C 211/50 | (2006.01) |
| C07C 245/08 | (2006.01) |
| C07D 213/80 | (2006.01) |
| C07D 307/30 | (2006.01) |
| C07D 307/68 | (2006.01) |
| C07D 401/04 | (2006.01) |
| C07D 403/14 | (2006.01) |
| C07D 407/04 | (2006.01) |

(56) References Cited

U.S. PATENT DOCUMENTS

2008/0008676 A1  1/2008  Janardanan Nair et al.
2012/0031634 A1  12/2012  Grison et al.

FOREIGN PATENT DOCUMENTS

| WO | 97/34714 A1 | 9/1997 |
| WO | 00/28093 A1 | 5/2000 |
| WO | 20111064462 A1 | 6/2011 |
| WO | 20111064487 A1 | 6/2011 |
| WO | 20131150197 A1 | 10/2013 |

OTHER PUBLICATIONS

Macadamia Conservation Trust, The four Macadamias, http://www.wildmacadamias.org.au/the-four-macadamias.*

Fernando et. al., Characterization of foliar manganese (Mn) in Mn (hyper)accumulators using X-ray absorption spectroscopy, 2010, New Phytologist, 188, 1014-1027.*

Fatiadi, The oxidation of organic compounds by active manganese dioxide, 1986, Plenum Press, pp. 119-260.*

Prabha K Padmavathiamma et al.: "Phytoremediation Technology: Hyper-accumulation Metals in Plants", Water. Al R. and Soil Pollution. Kluwer Academic Publishers. DO, vol. 184. No. 1-4, May 22, 2007 (May 22, 2017). pp. 105-126, XP019535063, ISSN: 1573-2932. DOI: 10.1007/S11270-007-9401-5 the whole document Plus particulierement: "2.4 Phytoextraction" et "3. Handling of hazardous biomass after phytoremediation" tables 4.5,7-9 p. 120. 1 eft-hand column. lines 13-24.

Stals M et al.: "Flash pyrolysis of heavy metal contaminated biomass from phytoremediation: Influence of temperature, entrained flow and wood/leaves blended pyrolysis on the behaviour of heavy metals", Journal of Analytical and Applied Pyrolysis, Elsevier BV, NL, vol. 87, No. 1, Jan. 1, 2010 (Jan. 1, 2010), pp. 1-7, XP026807617, ISSN: 0165-2370 [retrieved on Sep. 15, 2009] the whole document Plus particulierement: 2.3 Biomass and pyrolysis product streams characterization (dernier paragraphe) 3.3.1. Char 3.4. Leaching test.

Lievens C et al: "Study of the potential valorisation of heavy metal contaminated biomass via phytoremediation by fast pyrolysis: Part I. Influence of temperature, biomass species and solid heat carrier on the behaviour of heavy metals", Fuel, IPC Science ANO Technology Press, Gui Loforo, GB, vol. 87, No. 10-11, Aug. 1, 2008 (Aug. 1, 2008), pp. 1894-1905, XP022611182, ISSN: 0016-2361, DOI: 10.1016/J.Fuel.2007.10.021 [retrieved on Nov. 21, 2007] the whole document Plus particulierement: abrege 2.1. Materials, sample preparation and used equipment.

Yang J G et al.: "Heavy metal removal and crude bio-oil upgrade from Sedum alfredii Hance harvest using hydrothermal upgrading", Journal of Hazardous Materials, Elsevier, Amsterdam, NL, vol. 179. No. 1-3. Jul. 15, 2010 (Jul. 15, 2010). pp. 1037-1041. XP027044961, ISSN: 0304-3894 [retrieved on May 11, 2010] the whole document.

Yang et al: "Heavy metal removal and crude bio-oil upgrading from Sedum plumbizincicola harvest using hydrothermal upgrading process", Bioresource Technology, Elsevier Bv, GB, vol. 101. No. 19, Oct. 1, 2010 (Oct. 1, 2010). pp. 7653-7657. XP027089417, ISSN: 0960-8524 [retrieved on May 23, 2010] the whole document.

Hu P J et al.: "Tolerance, accumulation and distribution of zinc and cadmium in hyperaccumulator Potentilla griffithii", Environmental and Experimental Botany, Elsevier, Amsterdam, NL, vol. 66, No. 2, May 1, 2009 (May 1, 2009), pp. 317-325, XP026161711, ISSN: 0098-8472, DOI: 10.1016/J.ENVEXPBOT.2009.02.014 [retrieved on Mar. 13, 2009] 2.1 Plant material and growth conditions (presence de sulfate de manganese comme nutriment).

Zhang S et al.: "A newly found cadmium accumulatorMalva sinensis Cavan", Journal of Hazardous Materials, Elsevier, Amsterdam, NL, vol. 173, No. 1-3, Jan. 15, 2010 (Jan. 15, 2010), pp. 705-709, XP026782519, ISSN: 0304-3894, DOI: 10.1016/J.JHAZMAT.2009. 08.142 [retrieved on Sep. 4, 2009] the whole document.

Teofilo Vamerali et al.: "Field crops for phytoremediation of metal-contaminated land. A review", Environmental Chemistry Letters, Springer, Berlin, DE, vol. 8, No. 1, 30 Dec. 30, 2009 (Dec. 30, 2009), pp. 1-17, XP019765247, ISSN: 1610-3661 the whole document tables 4,6.

Guillaume Losfeld et al.: "Design and performance of supported Lewis acid catalysts derived from metal contaminated biomass for FriedelCrafts alkylation and acylation", Catalysis Today, Elsevier, NL, vol. 189, No. 1, Feb. 21, 2012 (Feb. 21, 2010), pp. 111-116, XP028400049, ISSN: 0920-5861, 001: 10.1016/J. ATTOD. 2012. 02.044 [retrieved on Mar. 5, 2010] the whole document Plus particulierement: 2.1 experimental table 1.

International Search Report, dated Oct. 29, 2013, from corresponding PCT application.

FR Search Report, dated Apr. 5, 2013, from corresponding FR application.

* cited by examiner

USE OF CERTAIN MANGANESE-ACCUMULATING PLANTS FOR CARRYING OUT ORGANIC CHEMISTRY REACTIONS

The invention relates to the use of plants that are accumulators of metals, more particularly of manganese, for implementing chemical reactions. From the point of view of synthesis, it makes it possible for the first time to carry out a whole series of mild oxidation reactions by means of reactive entities of vegetable origin that can advantageously replace the conventional oxidants of organic chemistry.

Moreover, the biological decontamination of soils contaminated with metals, metalloids, industrial and agricultural organic wastes and discharges or radioisotopes is a problem of great concern since the soil performs essential functions that largely determine the production of food products and water quality.

Among the different polluting substances, the heavy metals are among the most harmful compounds, as they are not biodegradable and they become concentrated in the ground. There are examples of sites in France, Belgium, Luxembourg, in the Jura, the Swiss Lower Alps or in the Pyrenees, just to mention the nearest regions, as well as in more distant regions such as New Caledonia, where nickel is more particularly exploited. Various African countries such as Gabon, Mali, South Africa, but also Mexico, China, India or Australia are also demonstrative examples.

Technologies for soil decontamination are difficult to develop, as it is a heterogeneous, complex and dynamic environment, which plays a key role as a buffer and processor of pollutants.

Various techniques of phytoremediation (phytoextraction, phytodegradation, phytostabilization, phytostimulation, phytotransformation, phytovolatilization and rhizofiltration) are currently in full development (Terry, N. and Banuelos G., editors, Phytoremediation of contaminated soil in water, Lewis Publishers, Boca Raton, Fla. 2000).

The Centre d'Ecologie Fonctionnelle et Evolutive (CEFE) (evolutionary and functional ecology centre) is investigating the phytostabilization technique, which consists of covering contaminated soils with plants capable of growing in the presence of heavy metals (this is called tolerance) (Frérot et al., Specific interactions between local metallicolous plants improve the phytostabilization of mine soils, Plant and Soil, 282, 53-65, 2006). Certain of these plant species that are used have the particular feature of accumulating metals in large quantity in their vacuoles (they are called hyperaccumulators). It is then a question of phytoextraction.

The team has studied two plants quite particularly; one, *Thlaspi caerulescens* (synonym *Noccaea caerulescens*), belonging to the Brassicaceae family, has remarkable properties of tolerance and hyperaccumulation of zinc, cadmium, and nickel. It concentrates them in the aerial parts (leaves and stems).

This plant is capable of storing zinc at concentrations 100 times greater than a conventional plant. Moreover, it is capable of extracting and concentrating zinc and cadmium in the aerial tissues, even on soils having a low concentration of these two metals.

In addition to their unusual tolerance for $Zn^{2+}$ and $Cd^{2+}$ and other metals, the hyperaccumulators are able to extract metals and transfer them to the aerial parts, where they become concentrated. For that reason, the roots contain very little heavy metals, in contrast to the plant species that are not accumulators. This triple property of tolerance/accumulation/concentration in the harvestable parts makes them a relevant tool in phytoremediation.

Moreover, the heavy metals are commonly used in organic chemistry as catalysts that are indispensable for carrying out chemical conversions that require a high activation energy. Thus, the role of the catalysts is to lower the energy barrier.

Their mechanism of action is often based on their Lewis acid properties. Zinc chloride is among those most used and is indispensable in many industrial and laboratory reactions. It is also often used in heterocyclic organic chemistry for catalysing many aromatic electrophilic substitutions.

It is also a catalyst of choice for carrying out hydrogenations of primary alcohols with the Lucas reagent, acetalization and aldolization reactions or cycloaddition reactions of the Diels-Alder type, etc.

Catalysts are also very useful in analytical electrochemistry, electrometallurgy and liquid-solid extraction, where there are numerous fields of application that are directly involved in different areas of economic life (batteries, cells and accumulators, detectors of spectroscopic apparatus, metallurgy, welding, etc.)

In international application WO 2011/064462 and application WO 2011/064487 published on 3 Jun. 2011, the invention of Professor Grison and of Doctor Escarré is described and claimed, relating to the use of a calcined plant or of a part of a calcined plant that has accumulated at least one metal in the M(II) form in particular selected from zinc (Zn), nickel (Ni) or copper (Cu), for the preparation of a composition containing at least one metal catalyst, the metal of which is one of the aforesaid metals in the M(II) form originating from said plant, said composition being devoid of chlorophyll, and allowing organic synthesis reactions involving said catalyst to be carried out.

As well as the species mentioned above (*Thlaspi caerulescens* now called *Noccaea caerulescens* and *Anthyllis vulneraria*), application WO 2011/064487 describes the use of many other metallophyte plants that are hyperaccumulators of heavy metals for the preparation of catalysts which can be used in organic chemistry.

Thus, the invention described in WO 2011/064487 concerns the use of a calcined plant or of a part of a calcined plant that has accumulated at least one metal in the M(II) form in particular selected from zinc (Zn), nickel (Ni) or copper (Cu) as defined above, in which said plant is in particular selected from the Brassicaceae family, in particular the species of the genus *Thlaspi*, in particular *T. goesingense, T. tatrense, T. rotundifolium, T. praecox*, the species of the genus *Arabidopsis*, in particular *Arabidopsis hallerii*, and of the genus *Alyssum*, in particular *A. bertolonii, A. serpyllifolium*, the Fabaceae family, the Sapotaceae family, in particular the species *Sebertia acuminata, Planchonella oxyedra*, the Convolvulaceae family, in particular the species *Ipomea alpina, Planchonella oxyedra*, the Rubiaceae family, in particular the species *Psychotria douarrei*, in particular *P. costivenia, P. clementis, P. vanhermanii*, the Cunoniaceae family, in particular the Geissois, the Scrophulariaceae family, in particular the species of the genus *Bacopa*, in particular *Bacopa monnieri*, the algae, in particular the red algae, in particular the *rhodophyta*, more particularly *Rhodophyta bostrychia*, the green algae or the brown algae.

Accordingly, the plant waste is directly utilized and transformed into "green" catalysts or into unconventional reagents.

In French patent application No. 12/52045 filed on 6 Mar. 2012 and not yet published, Professor Grison and the researchers Escande and Losfeld showed that, unexpectedly, certain other plants that belong to the genus *Sedum* as well as a different plant, *Potentilla griffithi*, have different metallophyte properties as hyperaccumulators of heavy metals, which make them particularly interesting for use in catalysis in organic chemistry.

The plants of the genus *Sedum* are succulent plants that belong to the Crassulaceae family, composed of more than 400 species. They have a natural capacity for growing on poor, dry soils, in an exposed environment and under difficult conditions. Their leaf system is fleshy and they are easy to grow.

Three species among them have developed unusual properties of extracting zinc and cadmium. *Sedum plumbizincicola* and *Sedum jinianum* have in particular a remarkable capacity for extracting zinc from contaminated soils in the south and the east of China. They have real potential for phytoextraction and are described as "plumbizincicolafor".

The properties of these metallophyte plants that are hyperaccumulators of heavy metals had already been the subject of several scientific publications, among which there may be mentioned:

1—L. H. Wu, N. Li, Y. M. Luo, Phytoextraction of heavy metal contaminated soil by *Sedum plumbizincicola* under different agronomic strategies, in: Proc. 5th Int. Phytotech. Conf., Nanjing, China, 2008, pp. 49e50.
2—L. H. Wu, S. B. Zhou, D. Bi, X. H. Guo, W. H. Qin, H. Wang, G. J. Wang, Y. M. Luo, *Sedum plumbizincicola*, a new species of the Crassulaceae from Zhejiang, China. Soils 38 (2006) 632e633 (in Chinese).
3—Longhua Wu, Changyin Tan, Ling Liu, Ping Zhu, Chang Peng, Yongming Luo, Peter Christie. 2012. Cadmium bioavailability in surface soils receiving long-term applications of inorganic fertilizers and pig manures. Geoderma, 173-174: 224-230
4—Ling Liu, Longhua Wu, Na Li, Yongming Luo, Siliang Li, Zhu Li, Cunliang Han, Yugen Jiang, Peter Christie. 2011 Rhizosphere concentrations of zinc and cadmium in a metal contaminated soil after repeated phytoextraction by *Sedum plumbizincicola*. International Journal of Phytoremediation, 13(8): 750-764
5—Jinping Jiang, Longhua Wu, Na Li, Yongming Luo, Ling Liu, Qiguo Zhao, Lei Zhang, Peter Christie. 2010. Effects of multiple heavy metal contamination and repeated phytoextraction by *Sedum plumbizincicola* on soil microbial properties. European Journal of Soil Biology, 46: 18-26
6—Ling Liu, Longhua Wu, Na Li, Cunliang Han, Zhu Li, J P Jiang, Yugen Jiang, X Y Qiu, Yongming Luo, 2009. Effect of planting densities on yields and zinc and cadmium uptake by *Sedum plumbizincicola*. Huan Jing Ke Xue, 30 (11): 3422-67
7—Longhua Wu, Yongming Luo, Xuerong Xing and Peter Christie. 2004. EDTA-enhanced phytoremediation of heavy metal contaminated soil and associated environmental risk. Agriculture, Ecosystems & Environment, 102(3): 307-318.

However, application of extracts of these plants as catalysts had never been described previously and forms the subject matter of French patent application No. 12/52045.

The inventors of the present application have now discovered that the richness of the soil in mineral species such as manganese may also be the cause of the gradual adaptation of plant communities, which become tolerant and hyperaccumulators of metallic trace elements, in particular Mn (II).

Examples of genera of plants comprising species that are hyperaccumulators of manganese are as follows:

*Alyxia, Azolla, Beauprea, Beaupreopsis, Bridelia, Crotalaria, Dicranopteris, Dipteris, Eugenia, Gleichenia, Gossia, Grevillea, Macadamia, Maytenus, Pinus, Spermacone, Stenocarpus, Virotia.*

These metallophyte species are thus capable of concentrating up to 110,000 ppm of manganese (based on dry matter) in their leaf system. Their ability to grow on eroded mining sites, depleted of organic matter and exposed to drought, makes these plants very useful for ecological remediation of sites damaged by intensive mining operations.

The cultivation of such species, for example those of the genus *Grevillea*, is of interest in addition to ecological remediation. They are a source of new Lewis acid catalysts and are very powerful oxidizing reagents, the reactivity of which can be adjusted by controlling the degree of oxidation of Mn and the composition of the medium. In the context of an environmental crisis and stricter European regulations for the chemical industry, the development of new, mild oxidizing systems that are effective and environmentally friendly is a real opportunity.

The treatments and preparations of the catalysts and oxidizing systems are simple, easy to implement, and comply with green and ecological constraints.

Therefore the first subject of the present application is the use, after heat treatment, of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus* or *Virotia* that has accumulated manganese (Mn) and optionally a metal or several metals in particular selected from magnesium (Mg), zinc (Zn), copper (Cu), iron (Fe), calcium (Ca), cadmium (Cd), aluminium (Al), for the preparation of a composition containing at least one mono- or polymetallic agent the metal or metals of which are selected from the metals originating from said plant, said composition being practically devoid of organic matter, for carrying out organic synthesis reactions involving said agent.

As indicated above, from the point of view of synthesis, the reactive entities of vegetable origin originating from the manganese accumulating plants mentioned above make it possible, in contrast to the plants cited in the applications indicated above, to carry out a whole series of mild oxidation reactions, and are capable of advantageously replacing the conventional oxidants used in organic chemistry.

By the expression "practically devoid of organic matter" is meant that the compositions of the invention contain approximately less than 10% by weight, preferably less than 5% by weight, and more preferably less than 2% by weight of carbon. In a preferred embodiment of the present invention, the compositions contain less than 0.2% and about 0.1% of carbon.

More particularly, the present application therefore relates to the use, after heat treatment, of a plant or of a part of a plant selected from the genus *Grevillea* and in particular *Grevillea exul* ssp. *rubiginosa*, *Grevillea exul* ssp. *exul* and *Grevillea gillivrayi* that has accumulated manganese (Mn) and optionally a metal or several metals in particular selected from calcium (Ca), magnesium (Mg), iron (Fe) or aluminium (Al) for the preparation of a composition containing at least one active mono- or polymetallic agent originating from said plant, said composition having previously been filtered and/or purified on resin and/or oxidized and/or fixed on a support and/or chelated and/or that has undergone electrolysis after acid treatment for carrying out organic synthesis reactions involving said agent.

More particularly, the present application therefore relates to the use of a composition prepared by the heat treatment of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Helanthius, Macadamia, Maytenus, Pinus, Spermacone, Stenocarpus, Virotia* or *Grevillea* that has accumulated manganese (Mn) and optionally a metal or several metals in particular selected from magnesium (Mg), zinc (Zn), copper (Cu), iron (Fe), calcium (Ca), cadmium (Cd), aluminium (Al) and containing at least one mono- or polymetallic agent, the metal or the metals of which are selected from the metals originating from said plant, said composition being practically devoid of organic matter, for carrying out organic synthesis reactions involving said agent as catalyst.

More particularly, the present application therefore relates to the use of a composition prepared by the heat treatment of a plant or of a part of a plant belonging to one of the genera selected from *Beauprea gracilis, Beauprea montana, Beaupreopsis paniculata, Garcinia amplexicaulis, Grevillea exul, Grevillea exul* ssp. *rubiginosa, Grevillea exul* ssp. *exul Grevillea gillivrayi, Grevillea meissneri, Maytenus fournieri drakeana, Maytenus fournieri fournieri, Spermacoce latifolia Aubl, Dicranopteris linearis* (synonym: *Gleichenia linearis*), *Bridelia ferruginea, Lantana camara, Psorospermum febrifugum Spach, Macadamia neurophylla, Phytolacca americana, Gossia bidwillii, Phytolacca acinosa Roxb, Virotia neurophylla, Macadamia integrifolia, Macadamia tetraphylla, Eleutherococcus sciadophylloides* (synonym *Acanthopanax sciadophylloides*), *Eleutherococcus sciadophylloides, Ilex crenata, Gossia bamagensis, Gossia fragrantissima, Gossia sankowsiorum, Gossia gonoclada, Maytenus cunninghamii, Chengiopanax sciadophylloides, Phytolacca americana, Austromyrtus bidwillii, Alyxia rubricaulia, Azolla caroliniana, Crotalaria semperflorens, Crotalaria clarkei, Dipteris conjugata, Eleutherococcus sciadophylloides, Ilex crenata, Eugenia clusioides, Pinus sylvestris, Stenocarpus ndnei, Virotia neurophylla, Schima superba, Polygonum hydropiper, Spermacoce latifolia Aubl, Dicranopteris linearis* (synonym: *Gleichenia linearis*), *Bridelia ferruginea, Lantana camara, Psorospermum febrifugum Spach*, that has accumulated manganese (Mn) and optionally a metal or several metals in particular selected from magnesium (Mg), zinc (Zn), copper (Cu), iron (Fe), calcium (Ca), cadmium (Cd), aluminium (Al) and containing at least one mono- or polymetallic agent, the metal or the metals of which are selected from the metals originating from said plant, said composition being devoid of organic matter, for carrying out organic synthesis reactions involving said agent as catalyst.

More particularly, the present application therefore relates to the use, after heat treatment, of a plant or of a part of a plant selected from *Beauprea gracilis, Beauprea montana, Beaupreopsis paniculata, Garcinia amplexicaulis, Grevillea exul, Grevillea exul* ssp. *rubiginosa, Grevillea exul* ssp. *exul Grevillea gillivrayi, Grevillea meissneri, Maytenus fournieri drakeana, Maytenus fournieri fournieri, Spermacoce latifolia Aubl, Dicranopteris linearis* (synonym: *Gleichenia linearis*), *Bridelia ferruginea, Lantana camara, Psorospermum febrifugum Spach, Macadamia neurophylla, Phytolacca americana, Gossia bidwillii, Phytolacca acinosa Roxb, Virotia neurophylla, Macadamia integrifolia, Macadamia tetraphylla, Eleutherococcus sciadophylloides* (synonym *Acanthopanax sciadophylloides*), *Eleutherococcus sciadophylloides, Ilex crenata, Gossia bamagensis, Gossia fragrantissima, Gossia sankowsiorum, Gossia gonoclada, Maytenus cunninghamii, Chengiopanax sciadophylloides, Phytolacca americana, Austromyrtus bidwillii, Alyxia rubricaulia, Azolla caroliniana, Crotalaria semperflorens, Crotalaria clarkei, Dipteris conjugata, Eleutherococcus sciadophylloides, Ilex crenata, Eugenia clusioides, Pinus sylvestris, Stenocarpus ndnei, Virotia neurophylla, Schima superba, Polygonum hydropiper, Spermacoce latifolia Aubl, Dicranopteris linearis* (synonym: *Gleichenia linearis*), *Bridelia ferruginea, Lantana camas, Psorospermum febrifugum Spach* and preferably the genus *Grevillea* and in particular *Grevillea exul* ssp. *rubiginosa, Grevillea exul* ssp. *exul* and *Grevillea gillivrayi* that has accumulated manganese (Mn) and optionally a metal or several metals in particular selected from calcium (Ca), magnesium (Mg), iron (Fe) or aluminium (Al) for the preparation of a composition containing at least one active mono- or polymetallic agent originating from said plant, said composition having been previously filtered and/or purified on resin and/or oxidized and/or fixed on a support and/or chelated and/or electrolyzed after acid treatment for carrying out organic synthesis reactions involving said agent as catalyst. The plants of the genus *Grevillea* and in particular *Grevillea exul* ssp. *rubiginosa, Grevillea exul* ssp. *exul* and *Grevillea gillivrayi* are the most abundant plants for the accumulation of manganese (Mn)

The extracts of the plants according to the present invention have a different composition of the mixtures of metals with respect to the extracts described in the application WO 2011/064487 and in the French application No. 12/52045 in that they contain a large quantity of manganese.

The presence of iron and of aluminium also proves to be very beneficial for many syntheses.

It also appears that the various metals present in the unpurified or partially purified mixtures display polymetallic synergy with one another, which allows these mixtures to be used in numerous reactions.

The properties of the mixtures originating from the plants according to the present invention make it possible to use them as very effective catalysts in a very great number of reactions, largely not envisaged in previous applications.

The present invention therefore also relates to the use as described above in which the mono- or polymetallic agent is a catalyst comprising manganese (Mn) having a degree of oxidation (II) (Mn (II)), or a degree of oxidation (III) (Mn (III)) and optionally a metal or several metals selected from magnesium (Mg), zinc (Zn), copper (Cu), iron (Fe), calcium (Ca), cadmium (Cd), aluminium (Al).

The present invention also relates to the use as described above in which the mono- or polymetallic agent is a reagent comprising manganese (Mn) having a degree of oxidation (III) (Mn (III)), or a degree of oxidation (IV) (Mn (IV)) and optionally a metal or several metals selected from magnesium (Mg), zinc (Zn), copper (Cu), iron (Fe), calcium (Ca), cadmium (Cd), aluminium (Al).

More particularly, the present invention relates to the use as described above, after heat treatment followed by an acid treatment and optionally oxidation and/or electrolysis of a plant or of a part of a plant selected from the genus *Grevillea* and in particular *Grevillea exul* ssp. *rubiginosa, Grevillea exul* ssp. *exul and Grevillea gillivrayi*, preferably *Grevillea exul* ssp. *exul* that has accumulated manganese (Mn) and optionally a metal or several metals selected from magnesium (Mg), zinc (Zn), copper (Cu), iron (Fe), calcium (Ca), cadmium (Cd), aluminium (Al).

It is to be understood that the plants can only accumulate manganese with a degree of oxidation (II) and that the presence of Mn with a degree of oxidations (III) or (IV)

results from oxidation reactions subsequent to the heat treatment of the plants or of a part of the plants.

In the various methods of use described above, the present invention relates in particular to the use in which the acid treatment is preferably carried out with hydrochloric acid, in particular gaseous HCl, 1N to 12N HCl, sulphuric acid, acetic acid, phosphoric acid, trifluoroacetic acid, trifluoromethanesulphonic acid, nitric acid, perchloric acid or para-toluenesulphonic acid.

In the various methods of use described above, the present invention relates in particular to the use in which the composition is filtered on an inert mineral solid such as Celite and optionally subsequently purified on an ion-exchange resin.

In the various methods of use described above, the present invention relates in particular to the use in which the concentration of Mn in the dried leaves of the plant *Grevillea exul* ssp. *exul* is preferably between about 15,000 and about 280,000 mg/kg of plant dry weight, the concentration of Fe(III) is between about 2,000 and about 35,000 mg/kg of plant dry weight and the concentration of Al(III) is between about 1,500 and about 80,000 mg/kg of plant dry weight.

The present invention also relates to a method for the preparation of a composition practically devoid of organic matter and comprising a metallic or polymetallic agent comprising manganese (Mn) having a degree of oxidation (II) (Mn (II)), a degree of oxidation (III) (Mn (III)) or a degree of oxidation (IV) (Mn (IV)) and optionally a metal or several metals selected from magnesium (Mg), zinc (Zn), copper (Cu), iron (Fe), calcium (Ca), cadmium (Cd), aluminium (Al), characterized in that it comprises the following steps:

a) Dehydration of the biomass of a plant or of a plant extract belonging to one of the genera selected from *Alyxia, Azolla, Beauprea, Beaupreopsis, Bridelia, Crotalaria, Dicranopteris, Dipteris, Eugenia, Gleichenia, Gossia, Helanthius, Macadamia, Maytenus, Pinus, Spermacone, Stenocarpus, Virotia* or *Grevillea* and in particular *Grevillea exul* ssp. *rubiginosa*, *Grevillea exul* ssp. *exul* and *Grevillea gillivrayi* that has accumulated manganese (Mn), and optionally a metal or several metals selected from magnesium (Mg), zinc (Zn), copper (Cu), iron (Fe), calcium (Ca), cadmium (Cd), aluminium (Al), b) Grinding the dry biomass of a plant or of a plant extract obtained in step a), c) Heat treatment in an oven, preferably at a temperature below 500° C., of the ground mixture and if desired and preferably, d) Treatment of the ash obtained in step c) with an acid preferably selected from hydrochloric acid, nitric acid, sulphuric acid, acetic acid or trifluoromethanesulphonic acid, nitric acid, perchloric acid or para-toluenesulphonic acid, phosphoric acid, trifluoroacetic acid followed, if desired, by dehydration of the solution or suspension obtained preferably under reduced pressure so as to obtain a dry residue and the solution or suspension obtained in step d) which, if desired, is subjected e) when the product obtained in step d) is a suspension, to a step of removal of the insoluble matter for example by filtration on an inert mineral solid such as Celite or by centrifugation, a step that is followed, if desired, by dehydration of the solution obtained preferably under reduced pressure so as to obtain a dry residue and/or f) to optional complete or partial purification on ion-exchange resins followed, if desired, by dehydration of the solution obtained preferably under reduced pressure so as to obtain a dry residue g) and the dry residue obtained in step c), d), e) or f) containing manganese with a degree of oxidation (II) (Mn (II)) which, if desired, in order to convert the manganese with a degree of oxidation (II) (Mn (II)) to manganese with a degree of oxidation (III) (Mn (III)) is subjected either to the action of dioxygen of the air in the presence of OH⁻ ions and then to treatment with an anhydride such as acetic anhydride or to the action of pyrrole optionally substituted in the presence of an aldehyde in order in order to obtain the formation of a porphinato-manganese complex with a degree of oxidation (II), which is subjected to the action of dioxygen of the air in order in order to obtain a complex with a degree of oxidation (III)

and the product obtained is subjected to dehydration preferably under reduced pressure in order in order to obtain a dry residue comprising manganese with a degree of oxidation (III) (Mn (III)) optionally associated with salts such as the chlorides, sulphates or acetates or oxides of at least one metal in particular selected from magnesium (Mg), zinc (Zn), copper (Cu), iron (Fe), calcium (Ca), cadmium (Cd), aluminium (Al)

h) and the product in dry form obtained in step c), d), e) or f) which, if desired, is subjected to the action of dioxygen of the air in the presence of OH⁻ ions in order to convert the manganese with a degree of oxidation (II) (Mn (II)) to manganese with a degree of oxidation (IV) (Mn (IV)) and, if desired, the suspension obtained is subjected to an acid treatment and then to dehydration preferably under reduced pressure so as to obtain a reagent practically devoid of manganese in the form $Mn_3O_4$ or $Mn_2O_3$ comprising manganese with a degree of oxidation (IV) (Mn (IV)) optionally associated with salts such as the chlorides or acetates or oxides of at least one metal in particular selected from magnesium (Mg), zinc (Zn), copper (Cu), iron (Fe), calcium (Ca), cadmium (Cd), aluminium (Al)

i) and the product in dry form obtained in step c), d), e) or f), which, if desired, is subjected to electrolysis in an acid medium in order in order to obtain manganese with a degree of oxidation (IV) (Mn (IV)) in the form of $MnO_2$ practically devoid of other metals j) and the product in dry form obtained in step c), d), e), f), g) or h), which, if desired, is mixed or treated in an acid medium with a support preferably selected from silica, montmorillonite, polygalacturonic acid, chitosan or a mixture of these products in order to obtain a supported catalyst k) and the product in dry form obtained in step c), d), e), f), g) or h), which, if desired, is reacted with ligands, preferably organic, optionally under the action of microwaves in order to obtain chelated agents, preferably catalysts, chelated for example with porphyrins.

The products obtained in step h) as well as the products comprising manganese with a degree of oxidation (IV) obtained according to the methods of the present invention are practically devoid of manganese in the form $Mn_3O_4$ or $Mn_2O_3$. This means that the oxidation products obtained, which are subjected to dismutation of the $Mn_3O_4$ and $Mn_2O_3$ to $MnO_2$ by return to pH=3 comprise in total less than 3% by weight of the two oxides $Mn_3O_4$ and $Mn_2O_3$.

In a preferred embodiment of the procedures for the preparation of the catalysts, the latter comprise steps that are common to all the preparations:

1. Dehydration of the biomass
2. Grinding the dry leaves, separating the stems and impurities The dried leaves then preferably undergo the following treatment, it being understood that certain steps may be omitted or carried out in a different order:

3. Grind the leaves briefly in a mortar.
4. Calcine the leaves in an oven so as to obtain the ash.
5. Grind the ash in a mortar in order to obtain a fine powder.
6. Digest with an acid.
7. Filter on a frit covered with Celite (to prevent clogging) with aspiration by a water-jet pump. Wash with acid.
8. Evaporate the polymetallic solution on an electric heater in a porcelain crucible under a fume hood.
9. Recover the solid phase from the crucible using a spatula and place the catalyst in the oven.

The solid may be used crude or partially purified depending on the required objectives.

In an alternative method for the preparation of the ash, the step or steps of dehydration and/or grinding of the leaves may be omitted and the leaves may be calcined directly by treatment between 300 and 500° C.

The ash may optionally be used directly if we wish to catalyse a reaction in basic catalysis using metal oxides.

The preferred conditions for carrying out these steps are as follows:

Dehydration of the biomass is carried out in an oven at a temperature of about 60° for 72 h.

The aforementioned heat treatment consists of calcining the biomass and especially the leaves in an oven at a temperature between 300 and 500° C., preferably 400°, for about 5 h, preferably working in successive stages.

The acid digestion or treatment of the ash obtained for example in step d) of the aforementioned method is implemented with acids in solution such as 1N to 12N HCl, gaseous HCl, sulphuric acid, acetic acid, $HNO_3$, trifluoromethanesulphonic acid (triflic acid or TfOH), para-toluenesulphonic acid, perchloric acid, suitable for the organic syntheses envisaged. About 15 to 20 ml of dilute acid (1M) or concentrated acid (up to 12M) per gram of ash is added to the reaction medium. The reaction medium is heated at about 60° C. with stirring for at least 2 h.

The solution obtained for example in step d) of the aforementioned method is optionally filtered on Celite or silica. Filtration is carried out on a frit for example of porosity 4 covered with about 3 cm of Celite (to prevent clogging) with aspiration by a water jet pump. The solution is then washed with concentrated hydrochloric acid and optionally concentrated under reduced pressure or lyophilized.

The optional partial purifications are preferably carried out on ion-exchange resins (for example Dowex 1) but it is also possible to use selective precipitations or methods of liquid-liquid extraction. The aim of these purifications is to remove cationic elements of physiological origin such as Na(I), K(I), Mg(II) and Ca(II), or species hyperaccumulated in the plants, such as Cd, Pb, Tl, which do not have beneficial reactivity and which may lower the reactivity of the catalyst.

It seems, however, to be important to maintain the polymetallic nature of the catalysts, even purified, as is confirmed by the results of organic synthesis, where the presence of various metals leads to a very beneficial synergy effect. The use of ion-exchange resins is the most suitable method for the purifications.

After passing over the ion-exchange resins, a selective precipitation may be envisaged.

The method of purification on ion-exchange resins is preferably carried out according to the following conditions:

Mn (II) may be fixed on the anion exchanger in a 12M HCl medium. K(I), Ca(II), Al(III), Mg(II), Ni(II) are thus separated.

Elution in HCl medium, 8M and then 6M, releases Mn (II).

Oxidation of the manganese with a degree of oxidation (II) (Mn (II)) to manganese with a degree of oxidation (III) (Mn (III)).

The originality of the method is the use of a natural oxidant, used under mild and environmentally friendly conditions: dioxygen. The redox reaction becomes possible if a basic pH is maintained. In fact, the redox potentials of the couples/pairs employed decrease with the pH, but not in parallel. At a pH above 7, the redox potential of the $O_2/H_2O$ couple/pair becomes greater than that of the Mn (III)/Mn (II) couple/pair.

The first step of the method is therefore to provide a basic medium by the addition of soda to convert $M_xCl_y$ to $M_x(OH)_y$, and more particularly $MnCl_2$ to $Mn(OH)_2$.

The optional oxidation of the dry residue obtained after acid treatment and optional filtration and/or purification, and containing manganese with a degree of oxidation (II) (Mn (II)) to manganese with a degree of oxidation (III) (Mn (III)) may therefore be carried out by the action of dioxygen of the air in the presence of OH⁻ ions preferably supplied by soda and then treatment with an excess of anhydride such as acetic anhydride. The products are obtained in the form of acetates with a degree of oxidation (III) after heating for about 30 minutes under reflux in water.

Another method that may be used for carrying out an optional oxidation of the dry residue obtained after acid treatment and optional filtration and/or purification, and containing manganese with a degree of oxidation (II) (Mn (II)) to manganese with a degree of oxidation (III) (Mn (III)) consists of allowing dioxygen of the air to act on a porphinato-manganese complex with a degree of oxidation (II). After the action of dioxygen of the air on this complex, a porphinato-manganese complex with a degree of oxidation (III) is obtained. The porphinato-manganese complex with a degree of oxidation (II) is obtained by reaction of pyrrole optionally substituted with a dry residue obtained after acid treatment and optional filtration and/or purification, and containing manganese with a degree of oxidation (II) (Mn (II)) in the presence of an aldehyde. This is preferably carried out in chloroform at ambient temperature with 4 equivalents of acetaldehyde or of benzaldehyde and 4 equivalents of pyrrole.

Then, for example, a product of formula is obtained

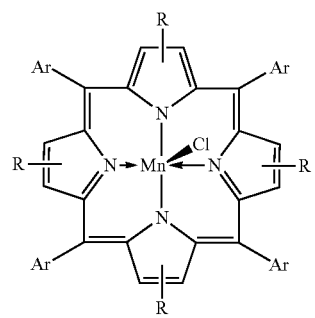

in which R=H, COOEt, CH$_2$COOEt, CH$_2$CH$_2$COOEt, CH$_3$, CH=CH$_2$, and Ar represents an aryl radical such as phenyl, p-chlorophenyl, p-toluyl.

Preparation of the Mn (IV) Oxidizing Reagent:

The optional oxidation of the dry residue obtained after acid treatment and optional filtration and/or purification, and containing manganese with a degree of oxidation (II) (Mn (II)) to manganese with a degree of oxidation (IV) (Mn (IV)) may be carried out by the strong action of dioxygen of the air at a basic pH of the order of 8 in the presence of soda to MnO$_2$, Mn$_3$O$_4$ and Mn$_2$O$_3$, followed by dismutation of the two last-mentioned oxides to MnO$_2$ by returning to pH=3 by the addition of hydrochloric acid of the order of 0.9 M.

Purification of the manganese salts is not necessary and the presence of the associated metal dichlorides such as FeCl$_3$ and AlCl$_3$, which activates MnO$_2$ in the oxidation reactions, is favourable.

After oxidation, the solid suspension is treated with concentrated HCl in order to redissolve the hydroxides.

MnO$_2$ is collected in the presence of other metal halides including FeCl$_3$.

Oxidation by the air is of the order of about 15 hours in the case of the controlled oxidation of Mn (II) to Mn (IV) by the dioxygen of the air. It is of the order of 30 minutes in the case of the controlled oxidation of Mn (II) to Mn (III).

The dry residue obtained after acid treatment and optional filtration and/or purification, and containing manganese with a degree of oxidation (II) (Mn (II)) may be subjected to electrolysis in an acid medium in order to obtain manganese with a degree of oxidation (IV) (Mn (IV)) in the form of MnO$_2$ practically devoid of other metals. A conventional oxidant of the pure MnO$_2$ type is obtained.

Electrolysis is carried out by an acid treatment of the biomass derived from *Grevillea exul exul* previously treated at 400° C., using sulphuric acid. Electrolysis is performed directly in a sulphuric medium using graphite electrodes. MnO$_2$ is recovered directly from the electrode by simple scraping.

The plant mineral extract thus obtained may then be used directly in unsupported catalysis or may be deposited on a support for use in supported catalysis (all other applications), depending on the requirements of the organic synthesis.

Unsupported Catalysis:

For homogeneous phase reactions, the catalysts are either used at the degree of oxidation existing during phytoextraction, or as co-catalysts or in oxidized form.

As indicated above, the solution is concentrated under reduced pressure and the dry residue is then stored under a protective atmosphere in order to prevent hydration, or even hydrolysis, of the Lewis acids present. The catalyst may be stored for several weeks without degradation before use.

Supported Catalysis:

Deposition on a support may be carried out under different conditions on one and the same support or on different supports.

For use of the catalysts according to the present invention in supported catalysis, mineral or organic supports may be used. Among the mineral supports, there may be mentioned the aluminosilicates, for example the zeolites, silica SiO$_2$, montmorillonite, alumina Al$_2$O$_3$, carbon, and metal oxides. It is also possible to use mixtures of the aforementioned supports as well as mine wastes such as aluminosilicates loaded with metal oxides.

Among the organic supports, there may be mentioned synthetic polymer resins and chiral organic polymers of natural origin such as cellulose, hemicellulose, alginate, tannic, polygalacturonic, tartaric, mandelic, quinic acids, or chitosan.

Depending on the support used, it is possible to prepare Lewis acid catalysts, Lewis acid/Brønsted acid mixed catalysts, catalysts for reduction and elongation of the carbon backbone.

The reactions that are preferably performed by supported catalysis are the aromatic electrophilic substitution reactions, protections and deprotections of functions, rearrangements, transpositions, aldolization and related reactions, reactions of dehydration, transfunctionalizations, constructions of heterocycles, multi-component reactions, depolymerizations, and redox reactions.

A catalyst may be prepared supported on a zeolite such as montmorillonite K10 starting for example from an unpurified plant extract preferably *Grevillea exul* ssp. *exul*.

In a preferred embodiment, a crude plant extract, preferably *Grevillea exul* ssp. *exul*, is introduced into an enamelled crucible heated beforehand to about 150° C. and montmorillonite is then added and ground until a homogeneous solid is obtained. The mixture is then heated for about a further 10 minutes prior to use in organic synthesis.

It is possible to replace the clay with silica, and use the same preparation method.

A Lewis acid/Brønsted acid catalyst may also be prepared supported on a zeolite such as montmorillonite K10 starting for example from an unpurified plant extract, preferably *Grevillea exul* ssp. *exul*.

In a preferred embodiment, a mixture of crude catalyst, preferably derived from *Grevillea exul* ssp. *exul* (Mn content: 58,983 ppm), montmorillonite K10 and 5 M hydrochloric acid is heated at about 70° C., with stirring.

After stirring at 70° C. for about 3 hours, the heating is increased to evaporate the medium. The solid obtained is stored in the oven (about 80-100° C. for one to two hours) in order to complete its dehydration and it is ground finely in the mortar. The final Mn content of the catalyst is about 60,000 ppm.

A Lewis acid/Brønsted acid catalyst may also be prepared supported on silica starting for example from an unpurified plant extract, preferably *Grevillea exul* ssp. *exul*.

In a preferred embodiment a mixture of catalyst preferably derived from *Grevillea exul* ssp. *exul* (Mn content: 58,983 ppm), silica (35-70 µm) and 5 M hydrochloric acid is heated at about 70° C., with stirring.

The same procedure is used as before for evaporating the medium in situ (under a fume hood, generally for one to two hours, or the medium is distilled using conventional distillation apparatus with an HCl trap, which reduces/prevents discharges of acid into the environment.

The final Mn content of the catalyst is about 60,000 ppm.

A catalyst may also be prepared supported on an SiO$_2$/polygalacturonic acid mixed support starting for example from an unpurified plant extract, preferably *Grevillea exul* ssp. *exul*.

The catalytic solution obtained after acid treatment is adjusted to pH=2 with 2M soda. The silica and the polygalacturonic acid, co-ground beforehand (the weight ratio may vary from 10/1 to 2/1), are added in solid form; the mixture is stirred for 30 minutes at ambient temperature, and then lyophilized; the solid obtained is used directly in organic synthesis.

Using the same method, the polygalacturonic acid may be replaced with chitosan.

In the present application, the expressions homogeneous catalysis and unsupported catalysis are to be regarded as having the same meaning. The same applies to the expressions: heterogeneous catalysis and supported catalysis.

An example of the preparation of chelated agents is given below in the experimental section by the preparation of ligands between manganese (II) and porphyrins. An example given below is the product of formula:

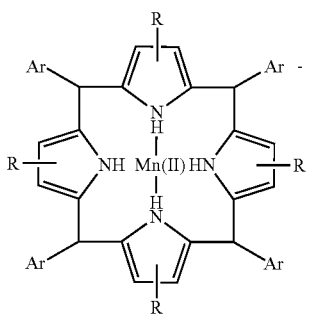

This product may be obtained under an inert atmosphere (nitrogen or argon) as it is oxidizable to Mn (III) by the dioxygen of the air.

The present invention in particular relates to a method for the preparation of a composition practically devoid of organic matter and comprising a metallic agent comprising manganese (Mn), having a degree of oxidation (II), (III) or (IV), and optionally a metal or several metals selected from calcium (Ca), magnesium (Mg), iron (Fe) or aluminium (Al), characterized in that the method is implemented starting from a plant or from a plant part selected from the genus *Grevillea* and in particular *Grevillea exul* ssp. *rubiginosa*, *Grevillea exul* ssp. *exul* and *Grevillea gillivrayi*, preferably *Grevillea exul* ssp. *exul*.

The present application also relates to the use of catalysts comprising Mn (II) obtained from extracts of metallophyte plants that are hyperaccumulators of Mn belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus, Virotia* for carrying out organic reactions, in particular the construction of heterocycles, the protection of carbonylated derivatives, preferably aldehydes and aromatic electrophilic substitutions, preferably the construction of porphyrins, Construction of Heterocycles The reactivity of the polymetallic system with concentrated $MnCl_2$ may be illustrated by the construction of heterocycles. Without wishing to be limited by any mechanistic explanation, the applicant considers that according to Pearson's hard soft acid base (HSAB) theory, $MnCl_2$ is a hard Lewis acid, capable of advantageously replacing $AlCl_3$, $FeCl_3$ and $BF_3$ in a certain number of multicomponent reactions such as the Biginelli reaction.

However, its use remains limited owing to low reactivity. The presence of other di- and trivalent cations intensifies the conventional reactivity of $MnCl_2$ and makes it useful in the preparation of heterocyclic structures. An example of the preparation of pyrimidones given below in the experimental section illustrates the Lewis acid properties of the polymetallic catalyst derived from *Grevillea*.

Protection of Carbonylated Derivatives

The mild Lewis acid properties of the green catalysts derived from *Grevillea* are also illustrated by a reaction of the acetalization-elimination type for example on citronellal catalysed by the catalytic system which is a subject of the present invention.

The reaction is specific to this vegetable catalytic system. The same reaction catalysed by an entity derived from a plant that is a hyperaccumulator of Zn(II) such as those described in French patent application No. 12/52045 gives an ene reaction spontaneously.

Aromatic Electrophilic Substitutions (ArES)

The Lewis acid catalysts according to the present invention, in particular when they are supported for example on montmorillonite, have a very useful activity in the reactions of aromatic electrophilic substitutions of the Friedel-Crafts alkylating and acylating type.

These results are unexpected, as very few examples of ArES are known with manganese dichloride: Mn (II).

The Lewis acid catalysts according to the present invention are very useful in electrophilic substitution reactions that employ fragile aromatic substrates. Thus, they are capable of catalysing the reaction of pyrrole with an aromatic aldehyde in order to form meso-tetraarylporphyrins, metallated or not metallated.

This method is unique and advantageously replaces the methods of Rothemund, Adler and Lindsey. It represents an important advance in the synthesis of free and metallated porphyrins, which are of increasing interest in research into mild anticancer treatments. Their natural property as photosensitizers is currently offering much hope in dynamic phototherapy.

Thus, it is possible to prepare meso-tetraphenylporphyrins of formula:

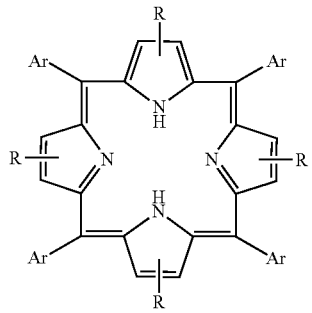

in which R=H, COOEt, $CH_2COOEt$, $CH_2CH_2COOEt$, $CH_3$, $CH=CH_2$, and Ar represents an aryl radical such as phenyl, p-chlorophenyl, p-tolyl.

Et represents an ethyl.

The present invention also relates to the use of one of the compositions containing at least one metal catalyst or preferably a polymetallic catalyst as described above in the implementation of organic synthesis reactions of functional conversions by Lewis acid catalysis selected from the aromatic electrophilic substitution reactions, the construction of heterocycles, the preparation and protection of carbonylated derivatives, radical oxidations, epoxidations, the oxidations of alcohols in the alpha position of a heterocyclic or carbocyclic aromatic group or of a double bond, the oxidizing cleavage of polyols, the oxidation of benzamines, oxidizing aromatic dehydrogenation of unsaturated and/or conjugated cyclic derivatives optionally comprising a heteroatom, the direct halogenation of enolizable compounds, the Hantzsch reaction in Lewis acid catalysis between an aldehyde, a beta-dicarbonylated compound and a source of ammonium leading to the formation of dihydropyridines (DHP).

It should be noted that the reactions of oxidizing cleavage of polyols and of oxidizing aromatic dehydrogenation of unsaturated cyclic derivatives are particularly important and unexpected.

The present invention also relates to the use of catalysts comprising Mn (III) which can be obtained from extracts of metallophyte plants that are hyperaccumulators of Mn either by the action of dioxygen of the air in the presence of $OH^-$ ions and then a treatment with an anhydride such as acetic anhydride or with the action of pyrrole optionally substituted in the presence of an aldehyde in order to obtain the formation of a porphinato-manganese complex with a degree of oxidation (II), which is subjected to the action of dioxygen of the air, optionally in the presence of one or more co-oxidants such as hydrogen peroxide, sodium hypochlorite, tert-butyl peroxide or phenyl ioxygen hypoiodite, for implementing organic reactions, in particular radical oxidations or oxidation of alkenes, in particular the epoxidation of alkenes.

The radical oxidants with a degree of oxidation (III) obtained by the action of dioxygen of the air in the presence of $OH^-$ ions and then a treatment with an anhydride such as acetic anhydride are very useful in organic synthesis as they avoid the preparation of halogenated derivatives and the use of toxic derivatives such as the trialkyl tin hydrides.

From a mechanistic point of view, the reagent comprising Mn (III) makes it possible to generate in situ a carbon-containing radical at the alpha position of an attractive group, which is then trapped in an intra- or intermolecular addition reaction. This principle is illustrated by the reaction of ethyl acetoacetate on styrene. The presence in particular of Cu(II) and of Fe(III) favourably accelerates the last step.

The principle of the reaction using the radical oxidants with a degree of oxidation (III) obtained by the action of pyrrole optionally substituted in the presence of an aldehyde in order to obtain the formation of a porphinato-manganese complex with a degree of oxidation (II), which is subjected to the action of dioxygen of the air, is that of biomimetic oxidation, where the porphyrin reproduces the oxidizing activity of the P-450 cytochromes.

The appeal and the originality of the system is that it is possible to use a catalytic system based on a mixed composition predominantly composed of porphyrin-Mn (III)/porphyrin-Fe (III), the most efficient oxidizing systems. The principle is based on the use of the natural composition of the hyperaccumulators of Mn described in the method indicated above.

These biomimetic and biosourced catalysts may be combined with many possible oxidants ($ClO^-$, PhIO, t-BuOOH, HOOH, etc.).

The olefins to be epoxidized are principally vinyl derivatives conjugated to an aromatic ring, where the ring may be mono- or disubstituted.

The present invention also relates to the use of catalysts comprising Mn (III) which can be obtained from extracts of metallophyte plants that are hyperaccumulators of Mn either by the action of dioxygen of the air in the presence of $OH^-$ ions and then a treatment with an anhydride such as acetic anhydride or with the action of pyrrole optionally substituted in the presence of an aldehyde in order to obtain the formation of a porphinato-manganese complex with a degree of oxidation (II), which is subjected to the action of dioxygen of the air, optionally in the presence of one or more co-oxidants such as hydrogen peroxide, sodium hypochlorite, tert-butyl peroxide or phenyl ioxygen hypoiodite, characterized in that the catalyst, preferably in the form of a porphinato-manganese complex with a degree of oxidation (III), is made to act on isoeugenol or ferulic acid preferably in acetonitrile in order to obtain vanillin.

An example of such a preparation using a porphinato-manganese complex with a degree of oxidation (III) is given below in the experimental section.

The present invention also relates to the use of catalysts comprising Mn (IV) practically devoid of manganese in the form $Mn_3O_4$ or $Mn_2O_3$, preferably comprising less than 3% of manganese in the form $Mn_3O_4$ or $Mn_2O_3$ and which can be obtained from extracts of metallophyte plants that are hyperaccumulators of Mn by the action of dioxygen of the air in the presence of $OH^-$ ions and, if desired, by an acid treatment and then dehydration preferably under reduced pressure so as to obtain a reagent comprising manganese with a degree of oxidation (IV) (Mn (IV)) optionally associated with salts such as the chlorides or acetates or oxides of at least one metal in particular selected from magnesium (Mg), zinc (Zn), copper (Cu), iron (Fe), calcium (Ca), cadmium (Cd), aluminium (Al) for implementing organic reactions, in particular:

A—the oxidations of alcohols located in alpha position of a heterocyclic or carbocyclic aromatic group or of a double bond, B—the oxidizing cleavage of polyols, C—the oxidation of benzamines, D—the oxidizing aromatic dehydrogenation of unsaturated and/or conjugated cyclic derivatives optionally comprising a heteroatom, E—the direct halogenation of enolizable compounds.

A—The Oxidations of Alcohols Located in Alpha Position of a Heterocyclic or Carbocyclic Aromatic Group or of a Double Bond The oxidation reactions of alcohols located in alpha position of a heterocyclic or carbocyclic aromatic group or of a double bond may be illustrated by the total oxidation of benzyl alcohol to benzaldehyde. An example of such a preparation is given in the experimental section. It should be noted that, under the same conditions, commercial $MnO_2$ only leads to traces of aldehyde! A reconstituted mixture of $MnO_2$ and Fe(III) only leads to 20% oxidation under the same conditions.

This example illustrates the advantage of using species that are hyperaccumulators of Mn (II) as a replacement for commercial $MnO_2$, the reactivity of which is very modest and finally is under-utilized. In the case of the vegetable system, the original and polymetallic composition of the medium makes it possible to intensify the oxidizing power of Mn (IV) while controlling the reaction up to the intermediate aldehyde stage.

From this point of view, the present invention also relates to the use of a reagent comprising Mn (IV) practically devoid of manganese in the form $Mn_3O_4$ or $Mn_2O_3$ [percentage to be defined] and optionally associated with salts such as the chlorides or acetates or oxides of at least one metal in particular selected from magnesium (Mg), zinc (Zn), copper (Cu), iron (Fe), calcium (Ca), cadmium (Cd), aluminium (Al) which can be obtained from extracts of a plant or of a part of a plant selected from the genus *Grevillea* and in particular *Grevillea exul* ssp. *rubiginosa, Grevillea exul* ssp. *exul* and *Grevillea gillivrayi* by the action of dioxygen of the air in the presence of $OH^-$ ions and, if desired, by an acid treatment and then by dehydration preferably under reduced pressure, characterized in that the reagent is made to act on (3-methoxy 4-hydroxy) benzene methanol preferably in ethyl acetate under reflux in order to obtain vanillin.

The oxidation of (3-methoxy 4-hydroxy) benzene methanol, or vanillic alcohol is also very effective with the reagent with a degree of oxidation (IV): Mn (IV). It leads directly to vanillin according to a green process of remarkable simplicity and efficiency.

This product has the most sought-after aroma in the world. The synthesis is totally biosourced:
- the alcohol precursor is a natural substance that is present and abundant in a certain number of plant species, such as Cotinus cogyggria,
- the oxidant is of totally natural origin, since it is prepared from plant extract. The vanillin thus synthesized may be described as vanillin with a natural aroma.

An example of such a preparation is given below in the experimental section.

This oxidation reaction is can easily be transposed to a controlled oxidation of allyl alcohols under similar conditions.

This possibility is illustrated with the example of geraniol, which leads to citral A (or geranial), which is in demand in the food industry for its lemon smell.

From this point of view, the present invention also relates to the use of a reagent comprising Mn (IV) practically devoid of manganese in the form $Mn_3O_4$ or $Mn_2O_3$ [percentage to be defined] and optionally associated with salts such as the chlorides or acetates or oxides of at least one metal in particular selected from magnesium (Mg), zinc (Zn), copper (Cu), iron (Fe), calcium (Ca), cadmium (Cd), aluminium (Al) which can be obtained from extracts of a plant or of a part of a plant selected from the genus Grevillea and in particular Grevillea exul ssp. rubiginosa, Grevillea exul ssp. exul and Grevillea gillivrayi by the action of dioxygen of the air in the presence of $OH^-$ ions and, if desired, by an acid treatment and then dehydration preferably under reduced pressure, characterized in that the reagent is made to act on geraniol in order to obtain geranial.

An example of such a preparation is given below in the experimental section.

B—The Oxidizing Cleavage of Polyols

The oxidation reaction, of great practical importance, is also possible on secondary alcohols of the benzyl type; the presence of the polyol system leads to an oxidizing cleavage that is rarely described with conventional manganese dioxide.

This reaction is to be noted and it is of very great reactivity; thus, it is completed after 5 h of stirring in dichloromethane at ambient temperature, without degradation and without competing reaction. It can therefore replace oxidizing reagents that are very aggressive or highly toxic ($Ce(NH_4)_2(NO_3)_6$ or $Pb(OAc)_4$). This result clearly shows the advantage of using a polymetallic oxidizing system derived from hyperaccumulators of manganese.

An example of such a preparation is given below in the experimental section.

C—The oxidation of Benzamines: Oxidation of Aniline:

The oxidation of aniline is a reaction of considerable industrial interest, but which is difficult and rarely unequivocal. However, it may lead to azobenzene, a very useful photosensitive compound. This reaction is still undergoing research intended to improve its preparation. The commonest method is based on the reduction of nitrobenzene in a basic medium and may lead to numerous by-products such as nitrosobenzene, 1,2-diphenylhydrazine, 1,2-diphenyl 1-oxide diazene and N-phenyl 1,4-benzenediamine.

An example of such a preparation that is given below in the experimental section shows that the oxidizing system GER-Mn (IV) allows a controlled oxidation to a single product, azobenzene (E/Z: 6/1), without the formation of by-products and directly, starting from aniline.

D—The oxidizing Aromatic Dehydrogenation of Unsaturated and/or Conjugated Cyclic Derivatives Optionally Comprising a Heteroatom This interesting use, of great practical importance, of the oxidizing system Mn (IV) generated from metallophytes allows the dehydrogenation of heterocycles, leading to the synthesis of aromatic structures.

A first example illustrating this possibility is given below in the experimental section.

Another example is the dehydrogenation of a natural cyclic terpene, α-terpinene, to an aromatic derivative, paramethyl cumene, a platform molecule of the chemical industry, which is also given below in the experimental section.

E—The Direct Halogenation of Enolizable Compounds.

One of the great advantages of the oxidizing system derived from Grevillea and comprising Mn (IV) is that it generates an oxidizing entity in the presence of mixed Lewis acids. This very particular mineral composition allows successive conversions to be carried out in situ. An example is the iodination of carbonylated compounds by the simple addition of alkaline iodide to the medium:

The reaction principle is based on:
- the oxidation of the iodide to diiodine by $MnO_2$ derived from GEE-Mn (IV);
- the enolization of the carbonylated compound by the dihalides that are present;
- the direct iodination of the enol thus formed.

All these steps are carried out successively, in situ, in a single reactor starting from the naturally available form of iodine, the iodides.

Examples of the iodination of ethyl acetoacetate and of cyclohexanone are given below in the experimental section.

The results obtained are remarkable and constitute a new green method for the easy iodination of carbonylated derivatives, which are usually of low reactivity. It avoids the use of dangerous and/or toxic reagents (oxone, mercuric chloride) and of diiodine.

F—The Synthesis of Pyridines by the Hantzsch Reaction—Oxidation in Situ

The Hantzsch reaction, involving an aldehyde, a beta-dicarbonylated compound and a source of ammonium, leads to the formation of dihydropyridines (DHPs), in Lewis acid catalysis. According to the conventional procedures, the DHPs obtained can be oxidized to pyridines, by means of oxidizing agents such as $KMnO_4$, $MnO_2$, $HNO_3$. The manganese-based catalysts have been shown to catalyse the two reactions very efficiently, in one pot, owing to the presence of traces of $Mn^{IV}$ (with oxidizing character) within the catalyst, essentially consisting of $Mn^{II}$, which catalyses the formation of DHP owing to its Lewis acid character. The use of the biosourced catalyst based on manganese therefore offers definite advantages in terms of catalytic efficiency, handling, reduction of the number of steps and of reagents used. Finally, the use of aggressive and polluting oxidizing agents is avoided.

The reaction conditions developed are perfectly compatible with the principles of green chemistry, since the reaction is completed in 5 minutes under microwave irradiation, in the solid phase, without using an organic solvent.

The reaction diagram is shown below:

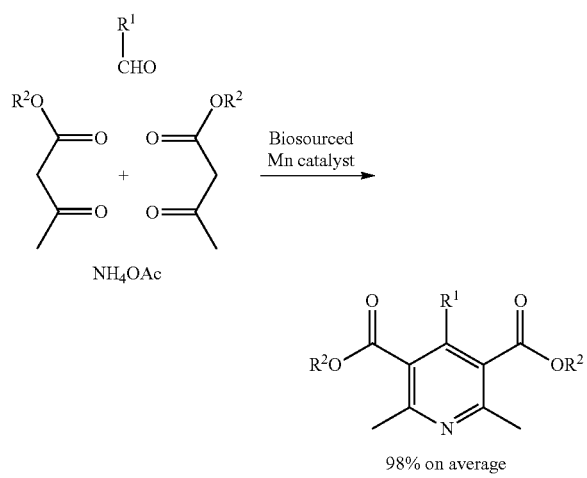

98% on average

Examples of Hantzsch reactions are given below in the experimental section.

G—The Epoxidation of Alkenes

It is possible to obtain the epoxide selectively from the starting alkene. The reaction is based on the formation of peroxymonocarbonate coordinated with the $Mn^{II}$ of the catalyst, the active species being produced from sodium hydrogen carbonate and hydrogen peroxide, reagents selected for their safety and their low environmental impact. The reaction leads to excellent epoxidation yields, sometimes above those stated in the literature for similar catalytic systems, over 4 h at 0° C. The alkenes, both enriched and depleted, are active in this reaction (although the yields are lower with the depleted alkenes).

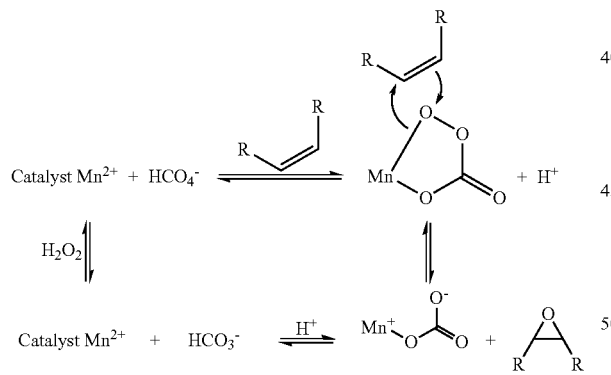

Examples of carrying out this reaction are given below in the experimental section.

H—The Synthesis of Vanillin

A new, very competitive synthesis of vanillin has been developed, due to the presence of several degrees of oxidation of Mn within the catalyst, each of them being involved in a particular step of the conversion. Whereas the conventional syntheses of vanillin starting from isoeugenol require the protection of the phenol, the oxidizing cleavage of the alkene and then the deprotection of the phenol, the biosourced Mn catalyst allows direct passage from isoeugenol to vanillin, in one pot, without protection/deprotection steps. The reaction takes place at ambient temperature and leads to a high yield (81%) of vanillin.

This example is typical of the synthetic possibilities of the method: in an acid medium, the epoxide is opened to diol, which is in its turn subjected to the oxidizing cleavage in situ. The epoxide is isolated in a mild basic medium.

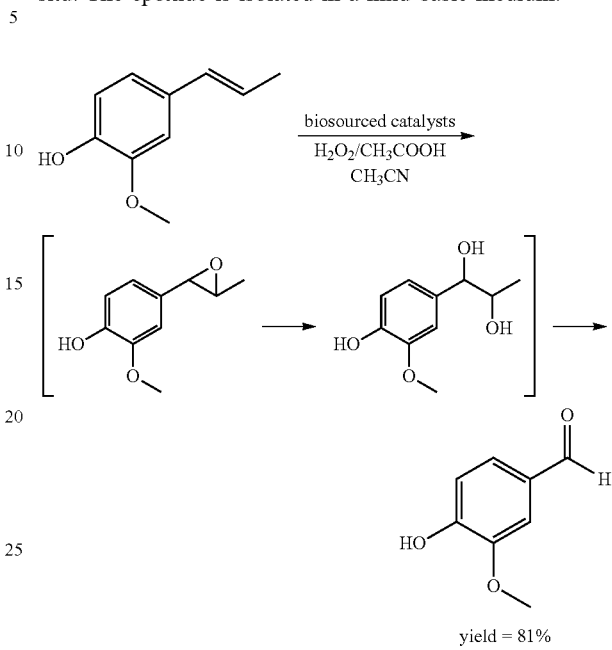

yield = 81%

An example of preparation is given below in the experimental section.

I—The Ene Reactions

Example

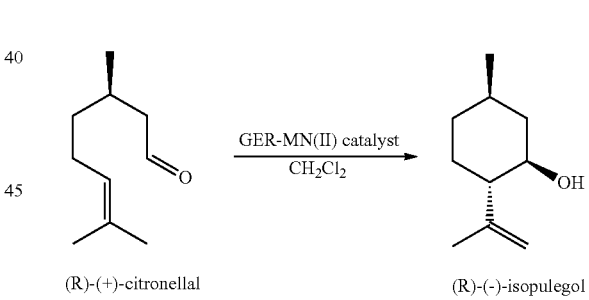

(R)-(+)-citronellal     (R)-(-)-isopulegol

Notes: industrial reaction, unsupported, and requiring the delicate preparation of $ZnBR_2$ and $ZnI_2$
GER: *Grevillea exul rubiginosa*

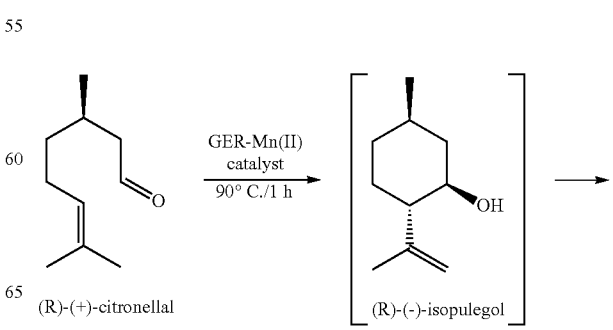

(R)-(+)-citronellal     (R)-(-)-isopulegol

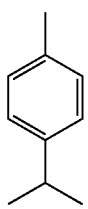
p-cymene

This possibility is specific to the Mn catalysts.

This evolution of isopulegol during its formation is unusual. This result is due to the presence of traces of Mn (IV) within the catalysts derived from *Grevillea exul rubiginosa*, making it possible to carry out the carbonyl-ene reaction, dehydration and aromatization in succession. It can be exploited for the direct synthesis of p-cymene, which is used in perfumery, cosmetics, pharmacy (expectorant and antitussive) and in organometallic catalysis.

An example of this preparation is given below in the experimental section.

In the description of the application given above and hereinafter including the claims, the expression "composition containing a catalyst" or "composition containing at least one catalyst" may be replaced by "catalyst".

The present application thus relates to the use, after heat treatment, of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus, Virotia* that has accumulated manganese (Mn) and optionally a metal or several metals in particular selected from magnesium (Mg), zinc (Zn), copper (Cu), iron (Fe), calcium (Ca), cadmium (Cd), aluminium (Al), for the preparation of a composition containing at least one metal catalyst, the metal of which is one of the aforesaid metals originating from said plant, said composition being practically devoid of chlorophyll or of organic matter, for carrying out organic synthesis reactions involving said catalyst.

The present application thus relates to the use, after heat treatment, of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus, Virotia* that has accumulated manganese (Mn) and optionally a metal or several metals in particular selected from magnesium (Mg), zinc (Zn), copper (Cu), iron (Fe), calcium (Ca), cadmium (Cd), aluminium (Al), for the preparation of a composition containing at least one metal catalyst, the metal of which is one of the aforesaid metals originating from said plant, said composition being practically devoid of chlorophyll, for implementing organic synthesis reactions involving said catalyst.

The present application thus relates to the use, after heat treatment, of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus, Virotia* that has accumulated manganese (Mn) and optionally a metal or several metals in particular selected from magnesium (Mg), zinc (Zn), copper (Cu), iron (Fe), calcium (Ca), cadmium (Cd), aluminium (Al), for the preparation of a composition containing at least one metal catalyst, the metal of which is one of the aforesaid metals in the form Mn (II) originating from said plant, said composition being devoid of chlorophyll or of organic matter, for implementing organic synthesis reactions involving said catalyst.

The present application also relates to a composition devoid of organic matter and in particular of chlorophyll containing at least Mn as catalyst in the form of chloride or sulphate, and cellulosic degradation fragments such as cellobiose and/or glucose, and/or glucose degradation products such as 5-hydroxymethylfurfural and formic acid and less than about 2% by weight, in particular less than about 0.2% by weight of C, in particular about 0.14% by weight.

In the present application, the expression devoid of organic matter signifies that the compositions according to the invention satisfy the criteria indicated above.

The present application also relates to the compositions such as are obtained by implementing the various methods described above.

The present application also relates to the use, after heat treatment, of a plant or of a part of a plant belonging to one of the genera selected from *Alyxia, Azolla, Beauprea, Beaupreopsis, Bridelia, Crotalaria, Dicranopteris, Dipteris, Eugenia, Gleichenia, Gossia, Grevillea, Helanthius, Macadamia, Maytenus, Pinus, Spermacone, Stenocarpus, Virotia* that has accumulated manganese (Mn) and optionally a metal or several metals in particular selected from magnesium (Mg), zinc (Zn), copper (Cu), iron (Fe), calcium (Ca), cadmium (Cd), aluminium (Al), for the preparation of a metal catalyst, the metal of which is one of the aforesaid metals originating from said plant, said catalyst being devoid of organic matter, for implementing organic synthesis reactions involving said catalyst.

As described below in the experimental section, the manganese content of the compositions of the invention may be between 15 000 and 270 000 ppm.

In the tables that are given in the present application, the values are stated in ppm unless stated otherwise.

EXAMPLES

The methods described in international application WO 2011/064462 and application WO 2011/064487 may also, in so far as required, be used for the preparation and the use of the plants and extracts of plants described in the present application.

Example 1: Procedures for the Preparation of the Catalysts

Steps that are common to all the preparations:
1. Dehydration of the biomass—oven at 60° C.—1 to 2 days, up to 72 hours (the progress of dehydration is monitored by weighing until the weight has stabilized)
2. Grinding of the dry leaves, preferably separating the stems and impurities The dried leaves then undergo the following treatment:
3. Briefly grind the leaves in a mortar
4. Calcine the leaves in an oven at 400° C. with a maximum temperature of 500° C. (programme with successive stages) for 5 h.
5. Grind the ash in a mortar in order to obtain a fine powder.
6. Digest with 12M HCl with magnetic stirring for about 12 h at 60° C.

7. Filtration on a frit of porosity 4 covered with 3 cm of Celite (to prevent clogging) with aspiration by a water jet pump. Wash with concentrated hydrochloric acid.
8. Evaporate (or distil) the polymetallic solution on an electric heater in a porcelain crucible under a hood.
9. Recover the solid phase from the crucible using a spatula and placed the catalyst in the oven (storage at 90° C.).

Table 1 below shows the composition of the solid residue before and after purification with ion-exchange resin, analyzed by ICP MS (Inductively Coupled Plasma Mass Spectroscopy). The resin is very selective for manganese. The purified catalyst is less depleted of Fe, Al and Zn than for the resins of type IRA 400.

The solid residue obtained is stored under nitrogen.

TABLE 1

Examples of mineral composition established by ICP MS from three species of the genus *Grevillea*, *Grevillea exul* ssp. *rubiginosa* (GER), *Grevillea exul* ssp. *exul* (GEE) and *Grevillea gillivrayi* (GG), one species of the genus *Dicranopteris*, *Dicranopteris linearis* (DL), *Pinus pinea*, (P) and *Spermacone latifolia* (SL) (values expressed in ppm of dry matter treated at 400° C. for 5 h, and then treated with 6N HCl at 60° C. for 12 h).

| | $^{24}$Mg | $^{27}$Al | $^{44}$Ca | $^{52}$Cr | $^{55}$Mn | $^{56}$Fe | $^{59}$Co | $^{60}$Ni | $^{63}$Cu | $^{66}$Zn | $^{75}$As | $^{114}$Cd | $^{121}$Sb | $^{137}$Ba | $^{208}$Pb |
|---|---|---|---|---|---|---|---|---|---|---|---|---|---|---|---|
| GER | 52595 | 2404 | 104359 | 311 | 26694 | 8961 | 14 | 448 | 159 | 562 | 81 | 6 | 3 | 117 | 75 |
| GEE | 46781 | 3926 | 109088 | 590 | 58983 | 18075 | 43 | 1175 | 154 | 666 | 70 | 12 | 4 | 232 | 67 |
| GG | 36017 | 5418 | 139690 | 245 | 58297 | 5419 | 20 | 3604 | 263 | 1026 | 10 | 49 | 3 | 120 | 289 |
| GG Pur. | 5306 | 1535 | 6203 | 678 | 261268 | 2278 | 36 | 867 | 88 | 262 | 14 | 43 | 2 | 35 | 230 |
| DL | 33498 | 48082 | 79889 | 149 | 33072 | 9224 | 66 | 590 | 165 | 3605 | 35 | 183 | 6 | 2782 | 174 |
| P | 33566 | 36835 | 78790 | 245 | 77897 | 30816 | 131 | 946 | 350 | 747 | 23 | 52 | 5 | 493 | 54 |
| SL | 32343 | 70324 | 67910 | 257 | 104860 | 16833 | 249 | 501 | 228 | 2153 | 20 | 174 | 0 | 532 | 37 |

The solid may be used crude or partially purified, depending on the sought objectives.

Example 1.1: Dehydration of the Biomass Between 300 and 500° C.

1 kg of leaves of *Grevillea exul* ssp. *exul* treated at 400° for 5 h gives about 150 g of ash.

At this stage, the ash may optionally be used directly if it is desired to catalyze a reaction in basic catalysis using metal oxides.

In all other cases, the ash is treated with acids in solution (for example HCl, HNO$_3$, trifluoromethanesulphonic acid) suitable for the organic syntheses envisaged.
1. 15 mL of acid, for example 1-12 M hydrochloric acid per g of ash, are introduced into the reaction mixture.
2. The reaction mixture is heated to 60° C. under stirring for at least 2 h.
3. The solution obtained is filtered on Celite or silica.

Example 1.2: Purification Using Dowex 1 Resin

This protocol for purification of the manganese catalysts is based on the use of a resin such as Dowex 1. In a 12M HCl medium, Mn (II) can be fixed on the anion exchanger. K(I), Ca(II), ARM), Mg(II), Ni(II) are thus separated. Elution in HCl medium, 8M and then 6M, releases Mn (II).

Protocol:
Allow 20 g of polystyrene-divinylbenzene resin Dowex-1 to swell in 12M HCl for 24 h. Pour 20 g of resin into a 0.03 cm$^2$ ion exchange column with a height of 20 cm. Wash this column with concentrated hydrochloric acid (12M) just before use.
Pour a solution in 12M hydrochloric acid medium, containing at most 500 mg of the elements to be separated, onto the column. Then elute Mn (II) with 100 ml of 8M hydrochloric acid and then with 100 ml of 6M hydrochloric acid (rate: about 0.5 cm/min (i.e. for 40 min)). Collect the various eluents of interest and evaporate them in order to obtain the solid catalyst. To be stored in a dry place (oven at 90° C.).

Examination of the various catalytic solids by X-ray fluorescence confirms these data and makes it possible to state that Mn is in the form Mn (II), Fe in the form Fe(III), Ni, Cu, Zn, Co, Cd, Pb, Ba, Mg, Hg and Mg with a degree of oxidation (II).

The counter-ions are predominantly chlorides, accompanied by the corresponding oxides.

The crude sample derived from *Grevillea exul*, originating from heat treatment of the biomass at 400° C. and having undergone an acid treatment with 1-10N HCl for 6-12 h, filtered on Celite and concentrated under vacuum at 100° C., is used directly without purification.

Example 2: Preparation of the Mn (III) Oxidizing Reagents

It is possible to generate oxidizing systems of different reactivity, not combined with the porphyrin ligands.

1st Method: The Mn (III) is Mainly in the Form MnX$_3$ (X Preferably Being OAc)

The conversion of manganese with a degree of oxidation (II) (Mn (II)) to manganese with a degree of oxidation (III) (Mn (III)), characterized in that manganese with a degree of oxidation (II) (Mn (II)) is subjected to the action of dioxygen of the air in the presence of OH$^-$ ions and then to treatment with an anhydride such as acetic anhydride, is carried out as follows:

The originality of the method lies in the use of a natural oxidant, which is used under mild and environmentally friendly conditions: dioxygen. The redox reaction becomes possible at basic pH. In fact, the redox potentials of the couples used decrease with the pH, but not in parallel. At pH above 7, the redox potential of the O$_2$/H$_2$O couple becomes greater than that of the Mn (III)/Mn (II) couple.

The first step of the method is therefore to make the medium basic by adding soda to convert M$_x$Cl$_y$ to M$_x$(OH)$_y$, and more particularly MnCl$_2$ to Mn(OH)$_2$.

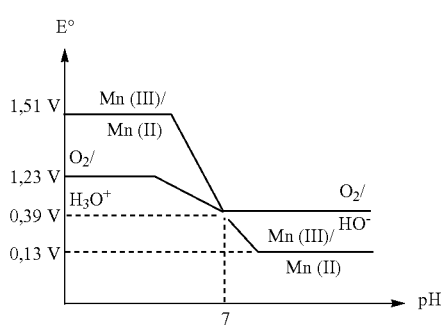

The presence of the other metallic species leads to consumption of hydroxyl ions, but does not interfere with the redox step, as all of the other transition metals are phyto-extracted at their maximum degree of oxidation ($Fe^{3+}$, $Cu^{2+}$, $Ni^{2+}$, $Zn^{2+}$, etc.).

Method:

1 g of GG (or GER, or GEE) catalytic solid is placed in a two-necked flask filled with 100 mL of degassed distilled water and placed under an inert atmosphere (nitrogen or argon). 700 mg of soda is then added gradually. Gentle bubbling with dioxygen is carried out until a quarter mole of gas has dissolved (monitored by weighing). The reaction is stopped after 30 minutes by adding a large excess of acetic anhydride, until an acid pH is obtained (pH=4). The dioxygen can no longer oxidize the Mn cations and the acetates derived from the transition metals are obtained after 30 minutes of heating under reflux. They are filtered, washed with acetic acid and dried under a nitrogen stream. GG-Mn (III) (or GER-Mn (III), GEE-Mn (III)) is then obtained.

2nd Method: G-Mn (III) with Ligand: this Possibility is Illustrated by the Example of the Preparation of the Metallated Porphyrins:

The conversion of manganese with a degree of oxidation (II) (Mn (II)) to manganese with a degree of oxidation (III) (Mn (III)), characterized in that manganese with a degree of oxidation (II) (Mn (II)) is subjected to the action of pyrrole optionally substituted in the presence of an aldehyde in order to obtain formation of a porphinato-manganese complex with a degree of oxidation (II), which is subjected to the action of dioxygen of the air and the product obtained is subjected to dehydration preferably under reduced pressure in order to obtain a dry residue comprising manganese with a degree of oxidation (III) (Mn (III)) optionally associated with salts such as the chlorides, sulphates or acetates or oxides of at least one metal in particular selected from magnesium (Mg), zinc (Zn), copper (Cu), iron (Fe), calcium (Ca), cadmium (Cd), aluminium (Al), is carried out as follows:

Example the porphyrins are prepared by the condensation of four equivalents of aldehyde and four equivalents of pyrrole. This reaction is carried out in $CHCl_3$, with a concentration of $10^{-2}$ M for the aldehyde substrates and the pyrrole. The GEE or purified-GEE catalysts are used at a concentration of $3.2 \times 10^{-3}$ M of Mn (II). The reaction mixture is stirred for 1 h at ambient temperature; it gets progressively darker. The flask contents are then poured into 100 mL of an iced aqueous solution (0° C.) of NaCl (30 g/100 mL). A green suspension appears. The mixture is filtered on a frit, and rinsed abundantly with water. The aqueous phase is extracted with 2×50 mL of ether, dried over $Na_2SO_4$, and then evaporated. A dark green solid is obtained. It is analyzed by UV-visible spectroscopy by observing the Soret bands and Q bands, and confirmed by $^1H$ NMR. The product obtained is chloro-meso-tetraphenylporphinato-manganese (III). It is obtained with a yield of 27% with purified GEE, which constitutes a clear improvement relative to the conventional methods, which require two steps and the overall yield of which varies between 3 and 18%. The supernatant obtained is of purple colour. If it is concentrated, meso-tetraphenylporphyrin is isolated, purified by chromatography and subjected to UV-visible analysis. The quantity obtained depends on the composition of the catalyst used. It is greater with unpurified GEE, the difference corresponds to the deficit of chloro-meso-tetraphenylporphinato-manganese (III). Thus, it is possible to orient the reaction towards manganic or free porphyrin by adjusting the composition of the catalyst derived from *Grevillea*.

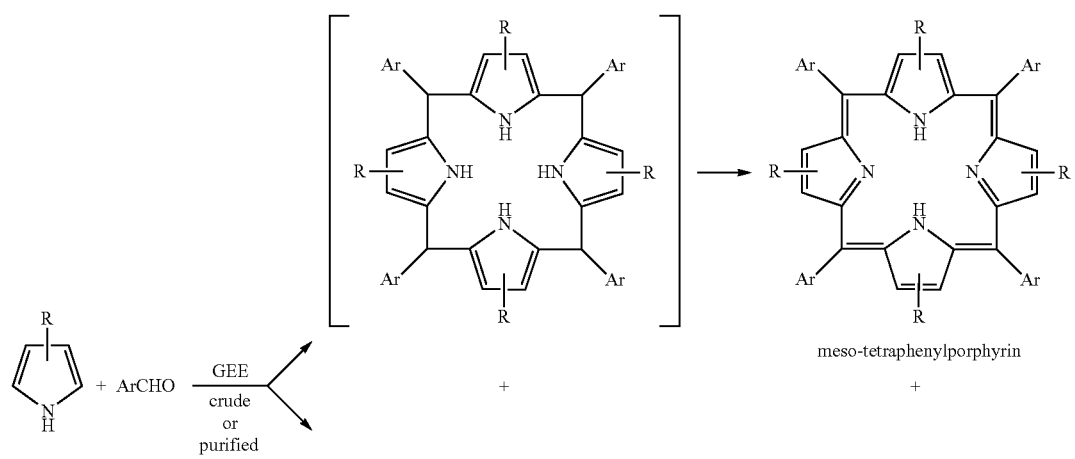

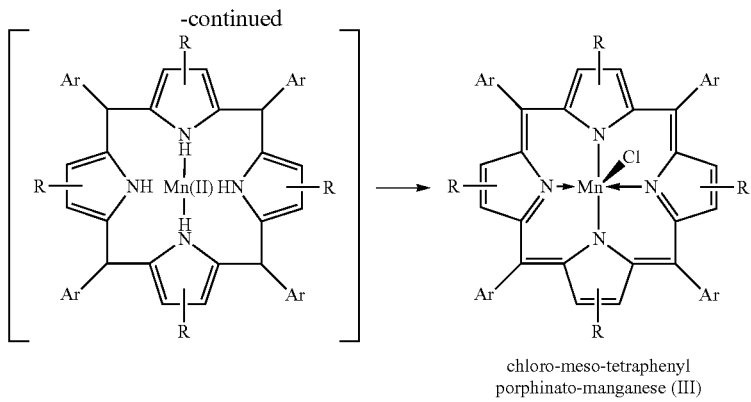

chloro-meso-tetraphenyl
porphinato-manganese (III)

|  | meso-tetraphenylporphyrin % | chloro-meso-tetraphenylporphinato-manganese(III) % |
|---|---|---|
| Crude GEE | 42 | 21 |
| GEE purified on resin | 6 | 27 |

Example 3

Example 3.1: Preparation of the G-Mn (III) Oxidizing Reagents

Type 1: G-Mn (III) with ligand: this possibility is illustrated by the example of the preparation of the metallated porphyrins in the preceding paragraph Type 2: G-Mn (III) where Mn (III) is mainly in the form $MnX_3$ (X preferably being OAc)

Example 3.2: The Controlled Oxidation of Phytoextracted Mn (II) to Mn (IV)

Preparation of the Mn (IV) Oxidizing Reagent

The objective here is to precipitate all of the metal cations, with an excess of HO-ions for manganese, and then to oxidize the obtained mixture in the air to degree (IV). This very advantageous method makes it possible to avoid the use of strong oxidants. Thus, the preferred method is the simplest possible, of low cost and without environmental impact. This is thorough the oxidation of phyto-extracted, isolated Mn (II) by the dioxygen of the air at pH=8 to $MnO_2$, $Mn_3O_4$ and $Mn_2O_3$, followed by the dismutation of the two last-mentioned oxides to $MnO_2$ by return to pH=3. Once again, the purification of the manganese salts is not required; on the contrary, the presence of the associated metal dichlorides such as $FeCl_3$ activates $MnO_2$ in the oxidation reactions.

After oxidation, the solid suspension is treated with concentrated HCl in order to redissolve the hydroxides. $MnO_2$ is collected in the presence of other metal halides, including $FeCl_3$. The oxidizing system is denoted G-Mn (IV).

Another alternative is the preparation of Mn (IV) by electrolysis, but the polymetallic composition is lost and a conventional oxidant of the pure $MnO_2$ type is obtained.

Example for a calcined sample of *Grevillea gillivrayi* dissolved in 0.20 M hydrochloric acid. The concentration of NaOH is such that the acid and the other cations, except magnesium, are hydroxylated quantitatively.

The volume of the solution subjected to oxidation is 250 mL. Oxidation by the air is stopped after about 15 hours (instead of 30 minutes as in the case of the controlled oxidation of Mn (II) to Mn (III)).

The solid suspension, ochre initially, becomes dark brown quite quickly. This coloration shows practically no change after the addition of 0.90 M HCl.

The appearance of blue coloration in a test in an ammoniacal medium shows that the copper hydroxide is redissolved. A previous test at pH 7 shows that all the manganese (II) has been converted; the oxidation is complete. The oxidizing system derived from *Grevillea gillivrayi* obtained is denoted GG-Mn (IV).

Example 4: Applications of the Agents in Organic Synthesis

Application, in organic synthesis, of the Mn (II) phyto-extracted as $MnCl_2$ associated with the metal chlorides obtained according to Table 1:

Example 4.1: Construction of Heterocycles

The reactions are carried out according to the following diagram:

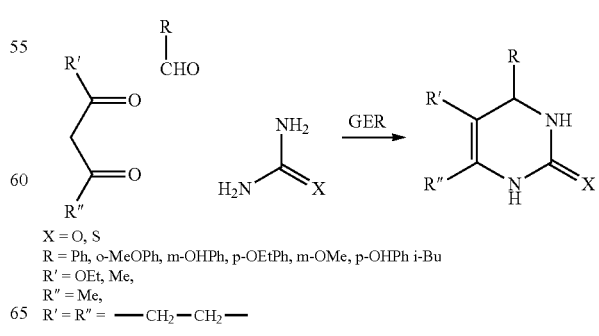

X = O, S
R = Ph, o-MeOPh, m-OHPh, p-OEtPh, m-OMe, p-OHPh i-Bu
R' = OEt, Me,
R" = Me,
R' = R" = —$CH_2$—$CH_2$—

| Species | | | |
|---|---|---|---|
| Catalyst *Grevillea exul rubiginosa* | aldehyde | beta-dicarbonylated compound | Urea/thiourea |
| Number of equivalents 0.20 | 2.0 | 2.0 | 1.0 |

Example

A, The catalyst derived from *Grevillea exul rubiginosa* GER (0.25 mmol of Mn) dispersed on 425 mg of montmorillonite K10, and then 2.5 mmol of benzaldehyde, 2.5 mmol of ethyl acetoacetate and 1.25 mmol of urea in 15 mL of ethanol are introduced into a flask equipped with a magnetic stirring bar, a condenser, a dropping funnel and a thermometer. The mixture is refluxed for 12 h. The reaction is monitored by TLC (development UV-eluent: dichloromethane/EtOAc), then the mixture is filtered and the filtrate is concentrated. The crude product is purified by crystallization from the EtOH/H$_2$O mixture, and then analyzed by $^1$H NMR, $^{13}$C NMR, COSY, HSQC and IR. The yield reaches 88%.

Example 4.2: Protection of Carbonylated Derivatives

The reactions are carried out according to the following diagram:

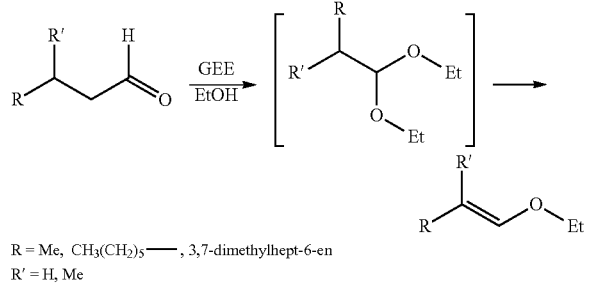

R = Me, CH$_3$(CH$_2$)$_5$——, 3,7-dimethylhept-6-en
R' = H, Me

| Species | | |
|---|---|---|
| Catalyst *Grevillea exul rubiginosa* | aldehyde | ethanol |
| Number of equivalents 0.10 | 1.0 | 85.7 |

Example 5 mL of absolute ethanol and the GER catalyst (0.30 mmol of Mn (II)) are introduced into a 25-mL flask equipped with a magnetic stirring bar, a condenser, a dropping funnel and a thermometer. Heat under reflux and stir, and then introduce 540 µL (462 mg, 3.0 mmol) of citronellal dropwise. Continue stirring and heating for 6 h, the reaction is complete. The reaction products may easily be analyzed by GC-MS and IR.

Example 4.3: Aromatic Electrophilic Substitutions

The reactions are carried out according to the following diagram:

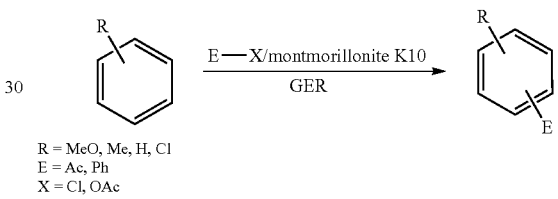

R = MeO, Me, H, Cl
E = Ac, Ph
X = Cl, OAc

Examples

| | | | |
|---|---|---|---|
| R = Cl | GER supported 1g/ | 0.32 eq. Mn/ | 2 h, 40° C., |
| E = Bn | on montmorillonite K10 1.5 g | BnCl | 100% |
| R = OMe | GER supported 1 g/ | 4 eq. Mn/ | 6 h, 70° C., |
| Er = Ac | on montmorillonite K10 1.5 g | Ac$_2$O | 80% |

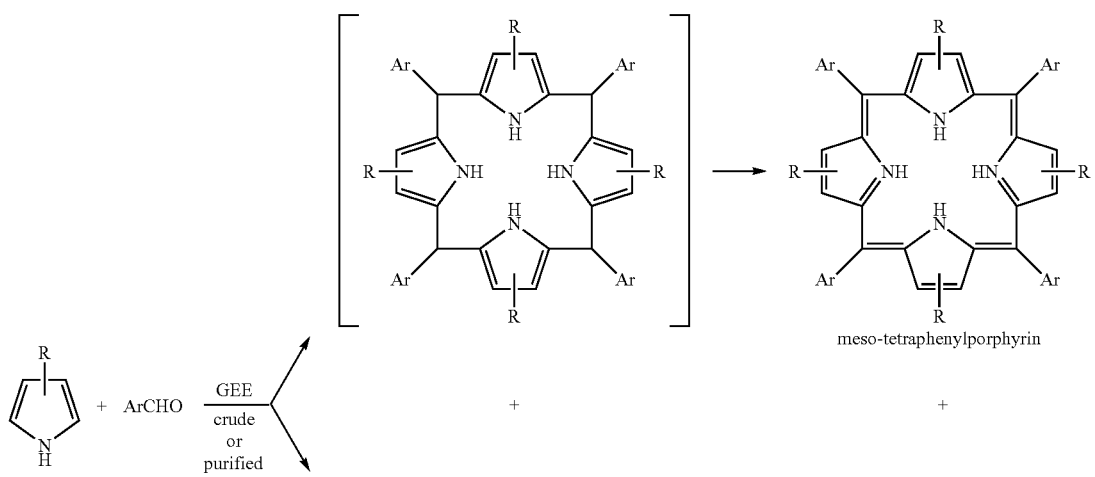

-continued

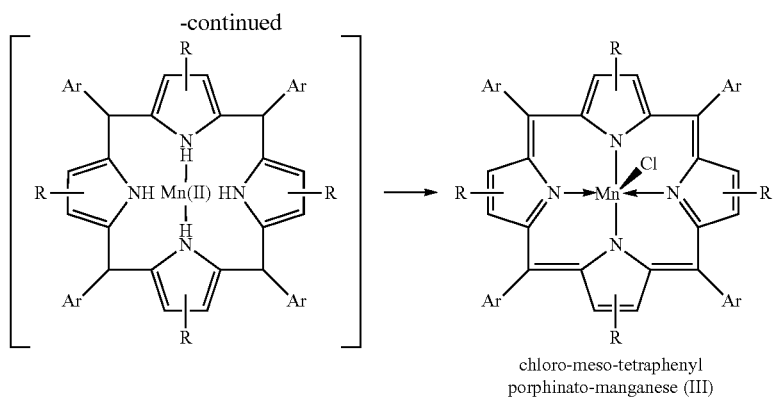

chloro-meso-tetraphenyl porphinato-manganese (III)

| Species | Catalyst *Grevillea exul exul* | aldehyde | Pyrrole |
|---|---|---|---|
| Number of equivalents | 0.32 | 4.0 | 4.0 |

Example

As indicated above, in the section describing the preparation of the Mn (III) reagents with ligands, the meso-tetraphenylporphyrin is isolated, purified by chromatography and subjected to UV-visible analysis. The quantity obtained depends on the composition of the catalyst used. It is greater with unpurified GEE, the difference corresponds to the deficit of chloro-meso-tetraphenylporphinato-manganese(III). Thus, it is possible to direct the reaction towards manganic or free porphyrin by adjusting the composition of the catalyst derived from *Grevillea*.

Example 4.4: Radical Oxidations Using the Mn (III) System of Vegetable Origin: Mn (III) Obtained by the 1st Method Given Above in Example 2

Radical oxidants of this kind are very useful in organic synthesis as they avoid the preparation of halogenated derivatives and the use of toxic derivatives such as the trialkyl tin hydrides.

From the mechanistic point of view, the green reagent G-Mn (III) makes it possible to generate in situ a carbon-containing radical in the alpha position of an attractive group, which is then trapped in an intra- or intermolecular addition reaction. This principle is illustrated by the reaction of ethyl acetoacetate on styrene. The presence in particular of Cu(II) and of Fe(III) accelerates the last step favourably.

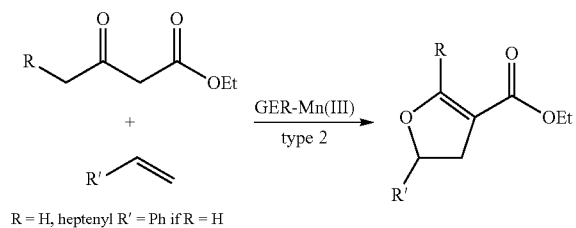

R = H, heptenyl R′ = Ph if R = H

| Species | Catalyst *Grevillea exul rubiginosa* | styrene | beta-dicarbonylated compound |
|---|---|---|---|
| Number of equivalents | 0.20 | 1.0 | 1.0 |

Example

An equimolar mixture (15 mmol) of ethyl acetoacetate and styrene is placed in 20 mL of acetic acid under a nitrogen atmosphere. GER-Mn (III) (3 equivalents of Mn) is added in one go. The mixture is heated to 45° C. and then stirred for one hour. It is diluted with water, and then extracted with ether, dried and concentrated. The product is purified by silica chromatography (hexane/Et$_2$O: 4/1) and analyzed by $^1$H NMR.

Example 4.5: Oxidations Catalyzed by the Tetraphenylporphinato-Metallated System, Mn (III) Obtained by the 2nd Method Indicated Above The principle of the reaction is that of biomimetic oxidation, where porphyrin reproduces the oxidizing activity of the P-450 cytochromes. The attraction and originality of the system is that it is possible to use a catalytic system based on a mixed composition predominantly composed of porphyrin-Mn (III)/porphyrin-Fe(III), the most efficient oxidizing systems. The principle is based on the use of the natural composition of the Mn hyperaccumulating plants described in the method of type 1-B. These biomimetic and biosourced catalysts may be combined with many possible oxidants (ClO⁻, PhIO), t-BuOOH, HOOH, etc.). The olefins to be epoxidized are mainly vinyl derivatives conjugated to an aromatic ring, where the ring may be mono- or disubstituted.

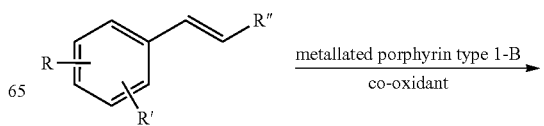

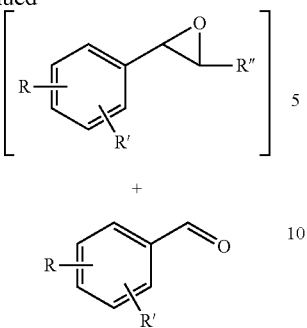

R = H, 3-O-alkyl
R' = H, 4-O-alkyl, OH
R" = H, alkyl, COOH

| Species | Catalyst porphyrin-Grevillea exul rubiginosa | alkene | co-oxidant |
|---|---|---|---|
| Number of equivalents | 0.10 | 1.0 | 1.0 |

Example 30 mmol of trans-methyl isoeugenol is diluted in 5 mL of acetonitrile. 10% of metallated porphyrins (type 2) are added, i.e. 3 mmol of active species (Mn (III)+Fe(III)), and then 30 mmol of 30% hydrogen peroxide. 3 drops of acetic acid are added, and then the mixture is stirred at 35° C. The progress of the reaction is monitored by GC MS. The reaction leads to 55% of dimethoxybenzaldehyde and 21% of epoxide, which can then be converted to dimethoxybenzaldehyde in a subsequent sequence (hydrolysis/treatment with G-Mn (IV)).

In the case where R=OMe, R'=OH and R"=Me, the method provides the most direct access to vanillin, based on a biomimetic process. The substrate, isoeugenol, and the oxidizing catalytic species [G-Mn (III)+Fe(III)] originate from natural resources and give access to a "natural" vanillin aroma.

Example 5: Uses of the Mn (IV) System of Vegetable Origin, in Organic Synthesis G-Mn (IV) allows the controlled oxidation of various organic functions:
A. Alcohols in the alpha position of an aromatic group (heterocycle or carbocycle), of a double bond,
B. Oxidizing cleavage of polyols,
C. Oxidation of benzamines,
D. Oxidizing aromatic dehydrogenation of unsaturated and/or conjugated cyclic derivatives bearing or not bearing a heteroatom,
E. Direct halogenation of enolizable compounds.

Example 5.1: Total Oxidation of Benzyl Alcohol to Benzaldehyde 1.15 mmol of alcohol, 1 g of catalyst and 25 mL of hexane are introduced into a single-necked flask under an inert atmosphere. The reaction is monitored by IR. The controlled oxidation of the alcohol to aldehyde is complete after reaction for 6 h. After filtration and washing of the solid with hexane, and then evaporation, the aldehyde is characterized by IR and $^1$H NMR.

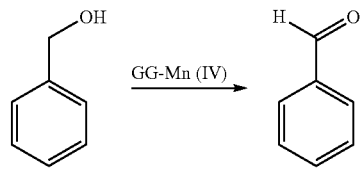 [SMILES: OCc1ccccc1 ; O=Cc1ccccc1]

Under the same conditions, commercial $MnO_2$ only leads to traces of aldehyde! A reconstituted mixture of $MnO_2$ and Fe(III) only leads to 20% oxidation under the same conditions. This example illustrates the advantage of using species that are hyperaccumulators of Mn (II) instead of commercial $MnO_2$, the reactivity of which is very modest and finally under-utilized. In the case of the vegetable system, the original polymetallic composition of the medium makes it possible to intensify the oxidizing power of Mn (IV) while controlling the reaction up to the intermediate aldehyde stage.

The oxidation of (3-methoxy 4-hydroxy) benzene methanol, or vanillic alcohol, is also very efficient with GEE-Mn (IV). Under-utilized

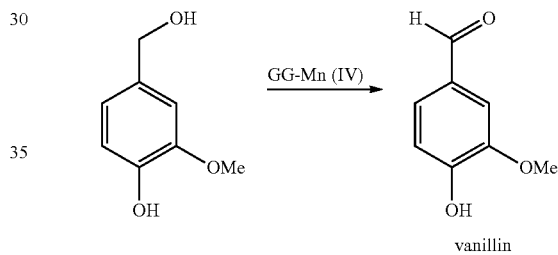

vanillin

| Species | Catalyst Grevillea gillivrayi Mn (IV) | alcohol |
|---|---|---|
| Number of equivalents | 0.54 | 1.0 |

Standard Protocol:
the alcohol (10 mmol) is placed in 20 mL of EtOAc under a nitrogen atmosphere. 500 mg of GEE-Mn (IV) catalytic solid is added in one go, and the mixture is stirred under reflux for 3 h. After filtration and concentration of the reaction medium, the medium is analyzed by IR and $^1$H NMR. The CO=vibration band of the ester function is located at 1713 cm$^{-1}$ and the aldehyde formed is located at 1673 cm$^{-1}$. A white product quickly crystallizes.

This reaction can be easily transposed to the controlled oxidation of allyl alcohols under similar conditions.

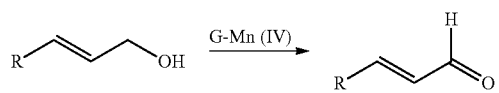

This possibility is illustrated with the example of geraniol, which leads to citral A (or geranial), which is sought after in the food industry for its lemon smell.

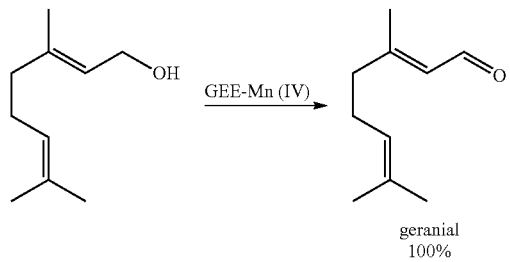

geranial
100%

Example 5.2: Controlled Oxidizing Cleavage of Polyols

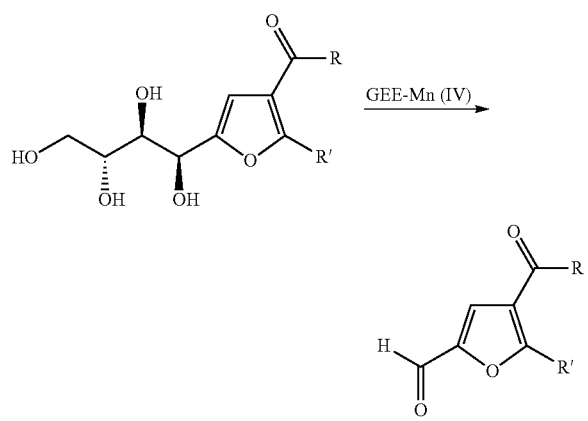

The reaction is complete after stirring for 5 h in dichloromethane at ambient temperature, without degradation and without competing reaction.

| Species | Catalyst *Grevillea gillivrayi* Mn (IV) | diol |
|---|---|---|
| Number of equivalents | 0.81 | 1.0 |

Protocol:

183 mg of furan derivative (R=OEt, R'=Me) is placed in 20 mL of $CH_2Cl_2$. 500 mg of GEE-Mn (IV) catalytic solid is added in one go, and the mixture is stirred. The reaction is monitored by IR. The C=O vibration band of the ester function is located at 1713 $cm^{-1}$ and the aldehyde formed is located at 2732 and 1687 $cm^{-1}$. The product crystallizes after filtration on Celite and evaporation. $^1$H NMR analysis confirms that the aldehyde formed is obtained, by the presence of a singlet at 9.7 ppm, deshielding of the aromatic proton at 7.5 ppm and disappearance of the polyol system.

Example 5.3: Oxidation of Benzamine: Example of Aniline

The Oxidation of Aniline is a Conversion of Industrial Interest

| Species | Catalyst *Grevillea gillivrayi* Mn (IV) | aniline |
|---|---|---|
| Number of equivalents | 1.5 | 1.0 |

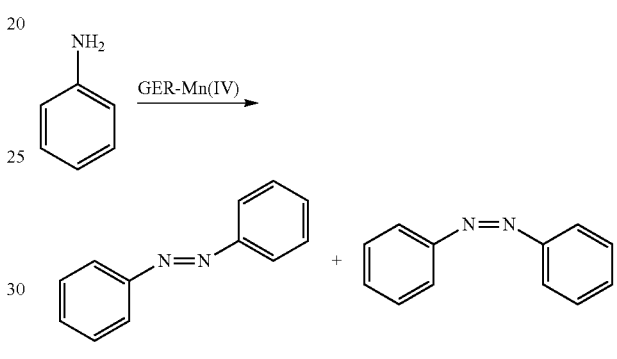

6 / 1

Protocol:

10 mmol of aniline is placed in 15 mL of ethyl acetate. GER-Mn (IV) (15 mmol of Mn (IV)) is added in one go. The mixture is refluxed and heated for 8 h. The solution gradually turns orange. This colour reflects formation of the required azobenzene. After filtration and concentration of the medium, azobenzene is obtained pure.

Example 5.4: Aromatizing Dehydrogenation of Heterocycles and Carbocycles

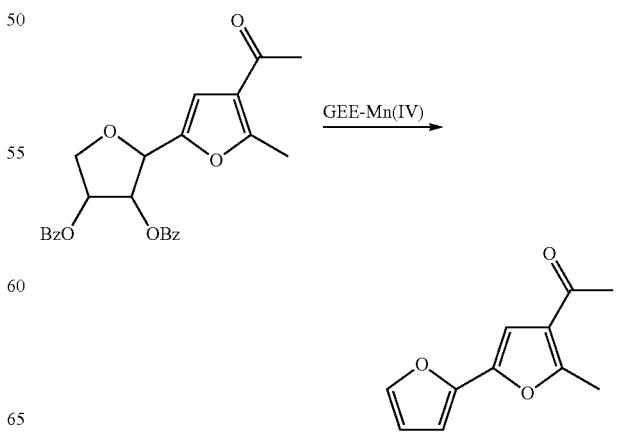

| Species | Catalyst Grevillea gillivrayi Mn (IV) | Derivative to be aromatized |
|---|---|---|
| Number of equivalents | 1.0 | 1.0 |

Method:

GEE-Mn (IV) (1.0 mmol of Mn (IV)) is added to a stirred solution of 420 mg (1.0 mmol) of benzoylated furan derivative, in 25 mL of toluene. The medium is stirred and heated under reflux for 12 h, and then filtered. The residual solid is washed with dichloromethane and then the filtrate is evaporated under reduced pressure. The crude product obtained is purified on a silica column, hexane/ethyl acetate elution, leading to a yield of 80% of difuran compound.

Another Example: Aromatizing Dehydrogenation of Carbocycles

Dehydrogenation of a natural cyclic terpene, alpha-terpinene, to an aromatic derivative, para-methyl cumene, which is a platform molecule of the chemical industry.

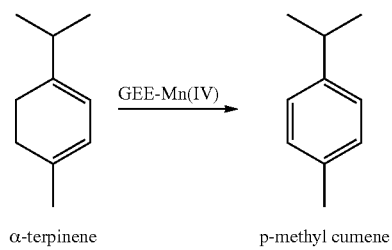

α-terpinene      p-methyl cumene

| Species | Catalyst Grevillea gillivrayi Mn (IV) | Derivative to be aromatized |
|---|---|---|
| Number of equivalents | 2.0 | 1.0 |

Method:

10 mmol of terpinene is placed in 15 mL of dichloromethane. GEE-Mn (IV) is added in one go at a rate of 2 molar equivalents of Mn (IV). The mixture is stirred for 12 h at 45° C., then filtered on Celite and concentrated under vacuum. The aromatic structure is easily confirmed by GC MS, IR and $^1$H NMR.

Example 5.5: Direct Halogenation of Enolizable Compounds

Example of the Iodination of Ethyl Acetoacetate:

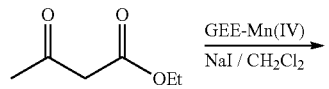

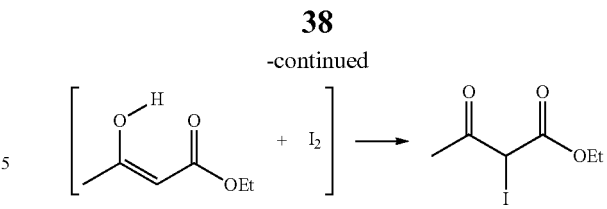

The conversion of ethyl acetoacetate is complete. Very fine GC MS analysis shows traces of ethyl iodoacetate, suggesting a possible iodination of ethyl acetate. This result is surprising as generally such a reaction is only described for compounds that are easily enolizable (alpha-ketoesters, diones, malonates, etc.: Organic Syntheses, Coll. Vol. 9, 310-314 (1998), L. F. Tietze and U. Beifuss). In order to verify this unexpected result, direct iodination by the one-pot oxidation sequence of the iodides to diiodine enolization-iodination of the enol was investigated with GER-Mn (IV) and cyclohexanone:

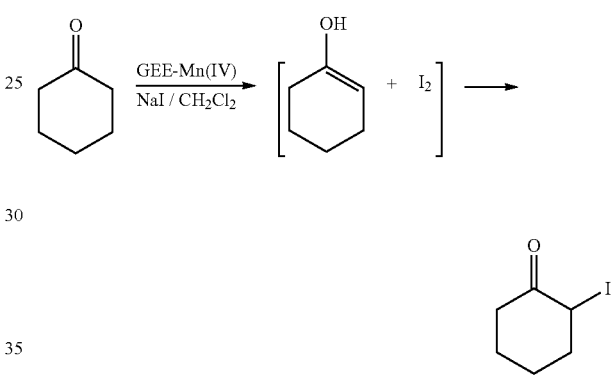

The reaction of direct iodination of cyclohexanone was carried out with a yield of 64%. This result is remarkable and constitutes a novel green method allowing the easy iodination of carbonylated derivatives, which are usually of low reactivity. It avoids the use of dangerous and/or toxic reagents (oxone, mercuric chloride) and of diiodine.

| Species | Catalyst Grevillea gillivrayi Mn (IV) | Substrate to be iodinated | Sodium iodide |
|---|---|---|---|
| Number of equivalents | 0.3 | 1.0 | 1.0 |

General protocol for the iodination of carbonylated derivatives and carboxylates: the substrate to be iodinated (10 mmol) diluted in 10 mL of dichloromethane, and sodium iodide (1 mmol) are placed in a 25-mL single-necked flask equipped with a condenser. The reagent GER-Mn (IV) (3 mmol of Mn (IV)) is added in one go and the mixture is stirred for 12 h at ambient temperature. The solution is filtered on Celite and the organic solution is washed with a solution of sodium thiosulphate, dried over sodium sulphate, filtered and concentrated under vacuum. The reaction is analyzed by GC-MS and then by $^1$H NMR.

Example 6: Synthesis of Pyridines by Hantzsch Reaction-Oxidation in Situ

Applying the following reaction diagram:

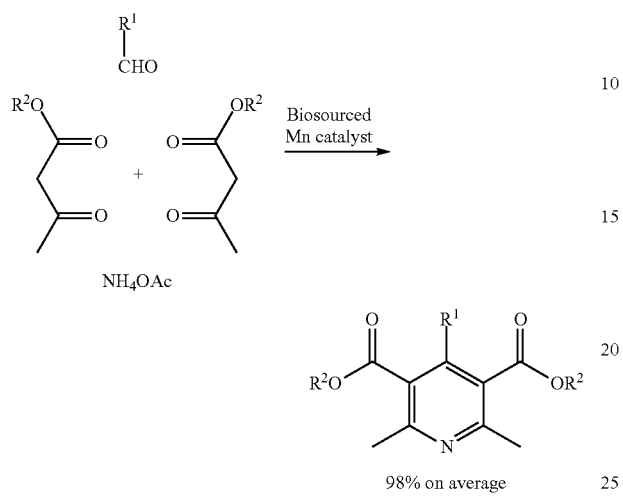

98% on average

| Species | Catalyst Grevillea exul rubiginosa | aldehyde | beta-dicarbonylated compound | Ammonium acetate |
|---|---|---|---|---|
| Number of equivalents | 0.10 | 1.0 | 2.0 | 1.5 | and the following procedure:

1 mmol of aldehyde, 2 mmol of ethyl acetoacetate, 1.5 mol of ammonium acetate and 0.1 mmol (manganese equivalent) of catalyst supported on $SiO_2$ (1:1 mass equivalent) are introduced into a scintillation tube. The mixture is placed in a 600 W microwave oven for 5 min (stirring after 1 min);

The following structures were obtained:

| Pyridine/yield (%) | Yield (%) |
|---|---|
| 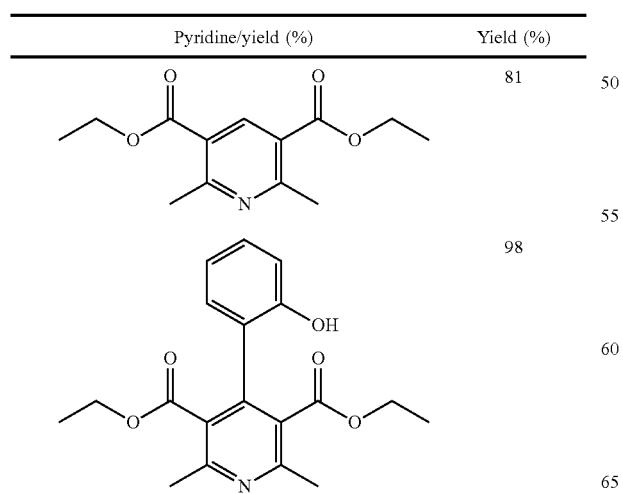 | 81 |
|  | 98 |

| Pyridine/yield (%) | Yield (%) |
|---|---|
|  | 92 |
|  | 99 |
|  | 69 |
|  | 98 |
|  | 96 |
|  | 98 |

-continued

| Pyridine/yield (%) | Yield (%) |
|---|---|
| [pyridine with 4-(4-ethoxyphenyl), 3,5-diethyl ester, 2,6-dimethyl] | 48 |
| [pyridine with 4-(pyridin-2-yl), 3,5-diethyl ester, 2,6-dimethyl] | 98 |
| [pyridine with 4-isobutyl, 3,5-diethyl ester, 2,6-dimethyl] | 98 |
| [pyridine with 4-ethyl, 3,5-diethyl ester, 2,6-dimethyl] | 98 |
| [pyridine with 4-butyl, 3,5-diethyl ester, 2,6-dimethyl] | 97 |
| [pyridine with 4-hexyl, 3,5-diethyl ester, 2,6-dimethyl] | 98 |
| [pyridine with 4-(pent-1-enyl), 3,5-diethyl ester, 2,6-dimethyl] | 98 |

-continued

| Pyridine/yield (%) | Yield (%) |
|---|---|
| [pyridine with 4-(1-methylhexyl), 3,5-diethyl ester, 2,6-dimethyl] | 95 |
| [pyridine with 4-(1-methylnonyl), 3,5-diethyl ester, 2,6-dimethyl] | 80 |
| [pyridine with 4-(citronellyl-type) substituent, 3,5-diethyl ester, 2,6-dimethyl] | 80 |
| [pyridine with 4-(geranyl-type) substituent, 3,5-diethyl ester, 2,6-dimethyl] | 98 |

Example 7: Epoxidation of Alkenes

Using the following standard conditions:

| Species | Catalyst *Grevillea exul exul* | alkene | NaHCO$_3$ | Hydrogen peroxide 30% |
|---|---|---|---|---|
| Number of equivalents | 0.05 | 1.0 | 0.2 | 3.2 |

1 mL of DMF, and the volume of water indicated for each alkene, are introduced into a haemolysis tube. The alkene (0.25 mmol) is added and the mixture is cooled to 0° C. in an ice bath, under stirring. The catalyst K10/*Grevillea exul exul* is then added in one go ($m_{(catalyst,\ in\ mg)}/n_{(alkene,\ in\ mmol)}=144$). Stirring is continued for 5 minutes, then a mixture of 30% $H_2O_2$ (85 μL; 0.8 mmol) and 0.2 M $NaHCO_3$ (250 μL; 0.05 mmol) previously stirred for 5 minutes, is added in 3 portions over 30 minutes. Stirring is continued at 0° C. for 4 h, then a sample is taken for extraction with ether and GC-MS analysis.

The following alkenes were thus epoxidized, with yields often greater than those described:

| Alkene[1] | Volume of water (μL)[3] | t(h) | T(° C.) | Yield of epoxide (%) |
|---|---|---|---|---|
| 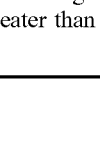 | 0 | 4 | 0 | 99 |
| 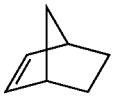 | 100 | 4 | 0 | 43 |
| 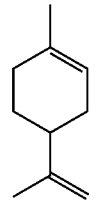 | 0 | 4 | 0 | 75 |
| 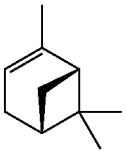 | 0 | 4 | 0 | 63 |
| 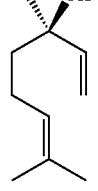 | 600 | 4 | 0 | 72 |
| 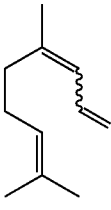 | 600 | 4 | 0 | 27 |
| 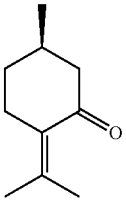 | 100 | 4 | 0 | 74 |

-continued

| Alkene[1] | Volume of water (μL)[3] | t(h) | T(° C.) | Yield of epoxide (%) |
|---|---|---|---|---|
| 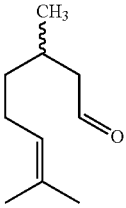 | 300 | 4 | 0 | 78 |
|  | 600 | 4 | 0 | 74 |
| 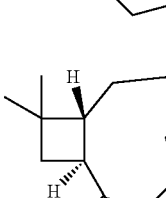 | 0 | 4 | 0 | 42 |
| 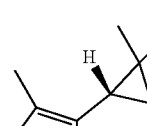 | 0 | 4 | 0 | 23 |
| 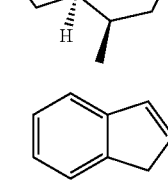 | 600 | 4 | 0 | 98 |
| 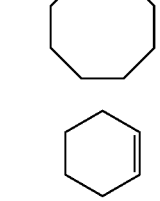 | 0 | 4 | 0 | 55 |
| 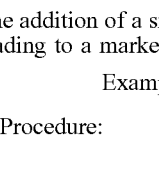 | 0 | 4 | 0 | 89 |

The addition of a small quantity of water proved beneficial, leading to a marked increase in yield in most cases.

Example 8: Synthesis of Vanillin

Procedure:

| Species | Catalyst *Grevillea exul rubiginosa* | isoeugenol | Hydrogen peroxide 30% | Acetic acid |
|---|---|---|---|---|
| Number of equivalents | 0.10 | 5.0 | 1.0 | 9.5 |

5 mL of acetonitrile, 30.5 µL (0.2 mmol) of isoeugenol, the appropriate weight of biosourced Mn catalyst, calculated so as to react 10% (in mol of limiting reagent) of the specific metallic species of the catalyst selected, 4.1 µL (0.04 mmol) of 30% hydrogen peroxide, 22 µL (0.38 mmol) of acetic acid and 4.66 µL (0.04 mmol) of acetophenone, which serves as internal standard, are introduced into a 25-mL flask. The mixture is stirred at AT for 48 h, and then analyzed by GC-MS. The yield of vanillin is 81%, based on the internal standard introduced.

Example 9: Ene Reactions

Summary of the operating conditions:

| catalyst/citronellal/ solvent | solvent | duration | % isopulegol | % p-cymene |
|---|---|---|---|---|
| 100 mg GER/ 154 mg (1 mmol, 1 equiv)/10 mL | $CH_2Cl_2$ | 1 h | 95 | 0 |
| 100 mg GER + $SiO_2$ 1 g/154 mg (1 mmol, 1 equiv) | — | 1 h | 5 | 80 |

| Species | Catalyst *Grevillea exul rubiginosa* | aldehyde |
|---|---|---|
| Number of equivalents | 0.05 | 1.0 |

Description of the Preparation of Isopulegol:

1 mmol of citronellal diluted in 10 mL of dichloromethane is added to a 25 mL four-necked flask equipped with a $CaCl_2$ trap, a thermometer, a magnetic stirring bar, a condenser and a dropping funnel. The GER catalyst (100 mg of catalyst, activated by heating at 150° C. for 15 min) is suspended in the solvent. The mixture is stirred for 60 minutes at 40° C. (the reaction is monitored by TLC (eluent: hexane/ether 4/1, development $I_2$)). The reaction mixture is filtered, the organic phase is washed with a hydrogen carbonate solution, dried and concentrated. The yield and stereoselectivity are determined by NMR and GC MS.

Description of the Preparation of P-Cymene:

The method is similar to the preceding method with 100 mg of catalyst supported on 1 g of silica, but the reaction is carried out without solvent at 90° C. for 1 hour. The conversion of isopulegol to p-cymene is easily monitored by GC MS.

The invention claimed is:

1. A method for implementing an organic synthesis reaction, comprising the following steps:
    a) preparing a composition containing at least one polymetallic agent, metals of which are selected from metals originating from a plant or a part of a plant, said composition containing less than 10% by weight of organic matter according to the following steps:
        i) dehydrating a plant or a part of a plant, said plant or said part of said plant belonging to a genus selected from the group consisting of *Alyxia, Azolla, Beauprea, Beaupreopsis, Bridelia, Crotalaria, Dicranopteris, Dipteris, Eugenia, Gleichenia, Gossia, Macadamia, Maytenus, Pinus, Phytolacca, Spermacone, Stenocarpus, Virotia* and *Grevillea*, that has accumulated manganese (Mn) and at least a metal selected from the group consisting of magnesium (Mg), iron (Fe), calcium (Ca) and aluminum (Al), and obtaining a dried plant or dried part of said plant;
        ii) grinding the dried plant or dried part of said plant obtained from step i), and obtaining a grinded mixture;
        iii) thermally treating the grinded mixture obtained for step ii) and obtaining the composition containing at least one polymetallic agent, said composition comprising Mn and at least a metal selected from the group consisting of Mg, Fe, Ca and Al;
    b) adding to a reaction mixture the composition obtained from step a); and
    c) implementing an organic synthesis reaction selected from the group consisting of radical oxidations, epoxidations, oxidations of alcohols located in an alpha position of a heterocyclic or carbocyclic aromatic group or of a double bond, oxidizing cleavage of polyols, oxidation of benzamines, and oxidizing aromatic dehydrogenation of unsaturated and/or conjugated cyclic derivatives optionally comprising a heteroatom, wherein the composition is a catalyst for the organic synthesis reaction.

2. The method according to claim 1, wherein the polymetallic agent is a catalyst comprising manganese (Mn) having a degree of oxidation (II) (Mn (II)), or a degree of oxidation (III) (Mn (III)).

3. The method according to claim 1, wherein the polymetallic agent is a reagent comprising manganese (Mn) having a degree of oxidation (III) (Mn (III)), or a degree of oxidation (IV) (Mn (IV)).

4. The method according to claim 1, wherein the thermally treating of step iii) is followed by an acid treatment step iv) and optionally oxidation and/or electrolysis of a plant or a part of a plant selected from the group consisting of *Grevillea exul* ssp. *Rubiginosa, Grevillea exul* ssp. *exul* and *Grevillea gillivrayi* that has accumulated manganese (Mn).

5. The method according to claim 4, wherein the acid treatment is carried out with hydrochloric acid, sulphuric acid, acetic acid, trifluoromethanesulphonic acid, nitric acid, perchloric acid, phosphoric acid, trifluoroacetic acid or para-toluenesulphonic acid.

6. The method according to claim 1, wherein the composition is filtered on an inert solid mineral and optionally subsequently purified on an ion-exchange resin.

7. The method according to claim 1, wherein the concentration of Mn is between 15,000 and 280,000 mg/kg of plant dry weight in dried leaves of the plant *Grevillea exul* ssp. *exul*.

8. The method according to claim 1, wherein the catalysts comprises Mn (II) obtained from extracts of metallophyte plants that are hyperaccumulators of Mn.

9. The method according to claim 1, wherein the catalysts comprises Mn (III) which can be obtained from a solution comprising extracts of metallophyte plants that are hyperaccumulators of Mn by either:
    action of dioxygen dissolved in the solution comprising the extracts, in the presence of OH⁻ ions in said solution comprising the extracts and then to a treatment with an anhydride, or
    action of pyrrole optionally substituted in the presence of an aldehyde in order to obtain the formation of a solution comprising a porphinato-manganese complex with a degree of oxidation (II), wherein the porphinatomanganese complex is subjected to action of dioxygen dissolved in said solution comprising the porphinatomanganese complex, optionally in the presence of one or more co-oxidants for carrying out an organic synthesis reaction.

10. The method according to claim 1, wherein the catalysts comprise Mn (IV) and contain less than 3% of manganese in the form $Mn_3O_4$ or $Mn_2O_3$ which can be obtained from a solution comprising extracts of metallophyte plants that are hyperaccumulators of Mn by action of dioxygen dissolved in the solution comprising the extracts, in the presence of $OH^-$ ions in said solution and, optionally, by an acid treatment and then to dehydration so as to obtain a reagent comprising manganese with a degree of oxidation (IV) (Mn (IV)).

11. The method according to claim 1, wherein a reagent comprising Mn (IV) and containing less than 3% of manganese in the form $Mn_3O_4$ or $Mn_2O_3$ which can be obtained from a solution comprising extracts of a plant or a part of a plant selected from the group consisting of Grevillea exul ssp. Rubiginosa, Grevillea exul ssp. exul and Grevillea gillivrayi by action of dioxygen dissolved in the solution comprising the extracts in the presence of $OH^-$ ions in said solution and optionally by an acid treatment and then dehydration is reacted with (3-methoxy 4-hydroxy) benzene methanol under reflux in order to obtain vanillin.

12. The method according to claim 1, wherein a reagent comprising Mn (IV) and containing less than 3% of manganese in the form $Mn_3O_4$ or $Mn_2O_3$ which can be obtained from a solution comprising extracts of a plant or a part of a plant selected from the group consisting of Grevillea exul ssp. Rubiginosa, Grevillea exul ssp. exul and Grevillea gillivrayi by action of dioxygen dissolved in the solution comprising the extracts in the presence of $OH^-$ ions in said solution and, optionally, by an acid treatment and then dehydration is reacted with geraniol in order to obtain geranial.

13. The method according to claim 1, wherein the composition comprises manganese (Mn) in the form Mn (II) in a quantity above 25,000 ppm, calcium (Ca), magnesium (Mg), iron (Fe) or aluminium Al(III).

14. The method according to claim 9, wherein the organic synthesis reaction is a radical oxidation or an oxidation of alkenes.

15. The method according to claim 10, wherein the organic synthesis reaction is selected from the group consisting of oxidations of alcohols located in alpha position of a heterocyclic or carbocyclic aromatic group or of a double bond, oxidizing cleavage of polyols, oxidation of benzamines, and oxidizing aromatic dehydrogenation of unsaturated and/or conjugated cyclic derivatives optionally comprising a heteroatom.

16. The method according to claim 1, wherein the composition contains less than 5% by weight of organic matter.

17. The method according to claim 4, wherein the composition, after acid treatment, has been subjected to at least one treatment selected from the group consisting of filtration, purification resin, oxidation, fixation on a support, chelation, and electrolysis.

18. The method according to claim 1, wherein said plant is selected from the group consisting of Beauprea gracilis, Beauprea montana, Beaupreopsis paniculata, Garcinia amplexicaulis, Grevillea exul, Grevillea exul ssp. rubiginosa, Grevillea exul ssp. exul Grevillea gillivrayi, Grevillea meissnerimeisneri, Maytenus fournieri drakeana, Maytenus fournieri fournieri, Spermacoce latifolia Aubl, Dicranopteris linearis (synonym: Gleichenia linearis), Bridelia ferruginea, Lantana camara, Psorospermun febrifugum Spach, Macadamia neurophylla, Phytolacca americana, Gossia bidwillii, Phytolacca acinosa Roxb, Virotia neurophylla, Macadamia integrifolia, macadamia tetraphylla, Eleutherococcus sciadophylloides (synonym Acanthonanax sciadophylloides), Eleutherococcus sciadophylloides, Ilex crenata, Gossia bamagensis, Gossia fragrantissima, Gossia sankowsiorum, Gossia gonoclada, Maytenus cunninghamii, Chengiopanax sciadophylloides, Phytolacca americana, Austromyrtus bidwillii, Alyxia rubricaulia, Azolla caroliniana, Crotalaria semperflorens, Crotalaria clarkei, Dipteris conjugata, Eugenia Clusioides, Pinus sylvestris, Stenocarpus ndnei, Virotia neurophylla, Schima superba, and Polygonum hydropiper.

19. A method for implementing an organic synthesis reaction, comprising the following steps:
a) preparing a composition containing at least one polymetallic agent, metals of which are selected from metals originating from a plant or a part of a plant, said composition containing less than 10% by weight of organic matter according to the following steps:
i) dehydrating a plant or a part of a plant, said plant or said part of said plant being selected from the genus consisting of Alyxia, Azolla, Beauprea, Beaupreopsis, Bridelia, Crotalaria, Dicranopteris, Dipteris, Eugenia, Gleichenia, Gossia, Macadamia, Maytenus, Pinus, Phytolacca, Spermacone, Stenocarpus, Virotia or Grevillea, that has accumulated manganese (Mn), and at least a metal selected from the group consisting of magnesium (Mg), iron (Fe), calcium (Ca) and aluminium (Al), and obtaining a dried plant or dried part of said plant;
ii) grinding the dried plant or dried part of said plant obtained from step i), and obtaining a grinded mixture;
iii) thermally treating the grinded mixture obtained for step ii) and obtaining the composition containing at least one polymetallic agent, said composition comprising manganese (II) and at least a metal selected from the group consisting of magnesium (Mg), iron (Fe), calcium (Ca) and aluminium (Al);
b) adding to a reaction mixture the composition obtained from step a); and
c) implementing an organic synthesis reaction selected from the group consisting of radical oxidations, epoxidations, oxidations of alcohols located in alpha position of a heterocyclic or carbocyclic aromatic group or of a double bond, oxidizing cleavage of polyols, the oxidation of benzamines, oxidizing aromatic dehydrogenation of unsaturated and/or conjugated cyclic derivatives optionally comprising a heteroatom, wherein the composition is a catalyst for the organic synthesis reaction.

20. A method for implementing an organic synthesis reaction, comprising the following steps:
a) preparing a composition containing at least one polymetallic agent, metals of which are selected from metals originating from a plant or a part of a plant, said composition containing less than 10% by weight of organic matter-according to the following steps:
i) dehydrating a plant or a part of a plant, said plant or said part of said plant being selected from the genus consisting of Alyxia, Azolla, Beauprea, Beaupreopsis, Bridelia, Crotalaria, Dicranopteris, Dipteris, Eugenia, Gleichenia, Gossia, Macadamia, Maytenus, Pinus, Phytolacca, Spermacone, Stenocarpus, Virotia or Grevillea, that has accumulated manganese (Mn), and at least a metal selected from the group consisting of magnesium (Mg), iron (Fe), calcium (Ca) and aluminium (Al), and obtaining a dried plant or dried part of said plant;

ii) grinding the dried plant or dried part of said plant obtained from step i), and obtaining a grinded mixture;

iii) thermally treating the grinded mixture obtained for step ii) and obtaining ashes;

iv) oxidation of the ashes obtained for step iii) and obtaining the composition containing at least one polymetallic agent, said composition comprising manganese (III) and/or manganese (IV) and at least a metal selected from the group consisting of magnesium (Mg), iron (Fe), calcium (Ca) and aluminium (Al);

b) adding to a reaction mixture the composition obtained from step a); and c) implementing an organic synthesis reaction selected from the group consisting of radical oxidations, epoxidations, oxidations of alcohols located in alpha position of a heterocyclic or carbocyclic aromatic group or of a double bond, oxidizing cleavage of polyols, the oxidation of benzamines, oxidizing aromatic dehydrogenation of unsaturated and/or conjugated cyclic derivatives optionally comprising a heteroatom, wherein the composition is a catalyst for the organic synthesis reaction.

21. The method according to claim 20, wherein the oxidation of step iv) is carried out by either:

action of dioxygen dissolved in a solution comprising the ashes obtained for step iii) in the presence of $OH^-$ ions in said solution, and then to a treatment with an anhydride, or action of pyrrole optionally substituted in the presence of an aldehyde in order to obtain the formation of a solution of a porphinato-manganese complex with a degree of oxidation (II), wherein the porphinato-manganese complex is subjected to action of dioxygen dissolved in said solution comprising the porphinato-manganese complex, or action of dioxygen dissolved in a solution comprising the ashes obtained for step iii) in the presence of $OH^-$ ions in said solution and, optionally, by an acid treatment.

* * * * *